US012195745B2

(12) United States Patent
Vandenberghe et al.

(10) Patent No.: US 12,195,745 B2
(45) Date of Patent: Jan. 14, 2025

(54) COMPOSITIONS AND METHODS FOR MODULATING TRANSDUCTION EFFICIENCY OF ADENO-ASSOCIATED VIRUSES

(71) Applicants: Massachusetts Eye and Ear Infirmary, Boston, MA (US); The Schepens Eye Research Institute, Inc., Boston, MA (US)

(72) Inventors: Luk H. Vandenberghe, Weston, MA (US); Amanda Dudek, Brookline, MA (US); Nerea Zabaleta Lasarte, Boston, MA (US)

(73) Assignees: Massachusetts Eye and Ear Infirmary, Boston, MA (US); The Schepens Eye Research Institute, Inc., Boston, MA (US)

( * ) Notice: Subject to any disclaimer, the term of this patent is extended or adjusted under 35 U.S.C. 154(b) by 814 days.

(21) Appl. No.: 17/269,955

(22) PCT Filed: Aug. 21, 2019

(86) PCT No.: PCT/US2019/047546
§ 371 (c)(1),
(2) Date: Feb. 19, 2021

(87) PCT Pub. No.: WO2020/041498
PCT Pub. Date: Feb. 27, 2020

(65) Prior Publication Data
US 2021/0317478 A1    Oct. 14, 2021

Related U.S. Application Data

(60) Provisional application No. 62/720,859, filed on Aug. 21, 2018.

(51) Int. Cl.
*C12N 15/86* (2006.01)
*A61K 47/64* (2017.01)
*C07K 14/005* (2006.01)
*C12N 7/00* (2006.01)

(52) U.S. Cl.
CPC .............. *C12N 15/86* (2013.01); *A61K 47/64* (2017.08); *C07K 14/005* (2013.01); *C12N 7/00* (2013.01); *C07K 2319/00* (2013.01); *C12N 2750/14121* (2013.01); *C12N 2750/14122* (2013.01); *C12N 2750/14143* (2013.01)

(58) Field of Classification Search
None
See application file for complete search history.

(56) References Cited

U.S. PATENT DOCUMENTS

| 6,855,314 | B1* | 2/2005 | Chiorini | C12N 15/86 |
| | | | | 435/320.1 |
| 7,271,002 | B2* | 9/2007 | Kotin | C12N 15/86 |
| | | | | 435/456 |
| 8,802,080 | B2* | 8/2014 | Warrington | C07K 14/005 |
| | | | | 435/456 |
| 10,081,659 | B2* | 9/2018 | Chiorini | A61K 48/0008 |
| 10,480,011 | B2* | 11/2019 | Gao | C12N 7/00 |
| 11,326,182 | B2* | 5/2022 | Paul | C07K 16/18 |
| 11,510,950 | B2* | 11/2022 | Keravala | C12N 7/00 |
| 11,698,377 | B2* | 7/2023 | Jin | G01N 30/7233 |
| | | | | 436/161 |
| 2009/0197338 | A1* | 8/2009 | Vandenberghe | A61P 31/12 |
| | | | | 435/320.1 |
| 2015/0376240 | A1 | 12/2015 | Cronin et al. | |
| 2018/0327752 | A1 | 11/2018 | Pillay et al. | |
| 2021/0292373 | A1 | 9/2021 | Agbandje-Mckenna et al. | |
| 2023/0048025 | A1* | 2/2023 | Nakai | A61B 5/16 |

FOREIGN PATENT DOCUMENTS

| EP | 1572893 | 9/2005 | |
| WO | WO 2005/072364 | 8/2005 | |
| WO | WO 2017/083423 | 5/2017 | |
| WO | WO-2017197355 A2 * | 11/2017 | ........... A61K 39/235 |
| WO | WO 2018/022608 | 2/2018 | |
| WO | WO 2018/035059 | 2/2018 | |
| WO | WO-2018035059 A1 * | 2/2018 | ........... C07K 14/005 |

OTHER PUBLICATIONS

Chen, C. L., Jensen, R. L., Schnepp, B. C., Connell, M. J., Shell, R., Sferra, T. J., Bartlett, J. S., Clark, K. R., & Johnson, P. R. (2005). Molecular characterization of adeno-associated viruses infecting children. Journal of virology, 79(23), 14781-14792. (Year: 2005).*
GenBank Accession No. AAU50364.1, Chen et al., Submitted Jul. 23, 2004 (Year: 2004).*
GenBank Accession No. QDH44190.1, Direct Submission, La Bella et al., Submitted Oct. 29, 2018 (Year: 2018).*
Bonten et al., "Lysosomal Protective Protein/Cathepsin A: Role of the "Linker" Domain in Catalytic Activation," The Journal of Biological Chemistry, Nov. 1995, 270(44):26441-26445.
D'Azzo et al., "Molecular defect in combined β-galactosidase and neuraminidase deficiency in man," Proc. Natl. Acad. Sci. USA, Aug. 1982, 79:4535-4539.
Deverman et al., "Cre-dependent selection yields AAV variants for widespread gene transfer to the adult brain," Nature Biotechnology, Feb. 1, 2016, 34:204-209.
Dong et al., "GPR108, an NF-κB activator suppressed by TIRAP, negatively regulates TLR-triggered immune responses," PLoS One, Oct. 17, 2018, 13(10):e0205303, 21 pages.
Dudek et al., "An Alternate Route for Adeno-associated Virus (AAV) Entry Independent of AAV Receptor," Journal of Virology, Apr. 1, 2018, 92(7):e02213-17, 15 pages.

(Continued)

Primary Examiner — Janet L Andres
Assistant Examiner — Carey Alexander Stuart
(74) Attorney, Agent, or Firm — Fish & Richardson P.C.

(57) ABSTRACT

Methods and compositions for modulating the transduction efficiency of an adeno-associated virus (AAV) into a cell or tissue are provided.

14 Claims, 21 Drawing Sheets
Specification includes a Sequence Listing.

(56) References Cited

OTHER PUBLICATIONS

Edgar, "Human GPR107 and murine Gpr108 are members of the LUSTR family of proteins found in both plants and animals, having similar topology to G-protein coupled receptors," DNA Sequence, Jun. 2007, 18(3):235-241.

Excoffon et al., "Directed evolution of adeno-associated virus to an infectious respiratory virus," PNAS, Mar. 10, 2009, 106(10):3865-3870.

Galjart et al., "Expression of cDNA encoding the human "protective protein" associated with lysosomal β-galactosidase and neuraminidase: Homology to yeast proteases," Cell, Sep. 9, 1988, 54(6):755-764.

Joung et al., "Genome-scale CRISPR-Cas9 knockout and transcriptional activation screening," Nature Protocols, Mar. 23, 2017, 12:828-863.

Kaludov et al., "Adeno-Associated Virus Serotype 4 (AAV4) and AAV5 Both Require Sialic Acid Binding for Hemagglutination and Efficient Transduction but Differ in Sialic Acid Linkage Specificity," Journal of Virology, Aug. 2001, 75(15):6884-6893.

Kaur, "Characterisation and Functional Analysis of GPR108, A Novel Golgi Protein," Thesis for the Degree of Doctor of Philosophy, Department of Biochemistry, National University of Singapore, Jan. 15, 2018, retrieved on May 27, 2021 from URL <http://scholarbank.nus.edu.sg/handle/10635/142828>, 273 pages.

Li et al., "MAGeCK enables robust identification of essential genes from genome-scale CRISPR/Cas9 knockout screens," Genome Biology, Dec. 5, 2014, 15:554, 12 pages.

Li et al., "Quality control, modeling, and visualization of CRISPR screens with MAGeCK-VISPR," Genome Biology, Dec. 16, 2015, 16:281, 13 pages.

Lock et al., "Rapid, Simple, and Versatile Manufacturing of Recombinant Adeno-Associated Viral Vectors at Scale," Human Gene Therapy, Sep. 24, 2010, 21(10):1259-1271.

Meindl et al., "Inhibition of neuraminidase activity by derivatives of 2-deoxy-2,3-dehydro-N-acetylneuraminic acid," Virology, Apr. 1974, 58(2):457-463.

PCT International Preliminary Report on Patentability in International Appln. No. PCT/US2019/047546, dated Mar. 4, 2021, 11 pages.

PCT International Search Report and Written Opinion in International Appln. No. PCT/US2019/047546, dated Jan. 27, 2020, 21 pages.

Pillay et al., "An essential receptor for adeno-associated virus infection," Nature, Jan. 27, 2016, 530:108-112, 17 pages.

Sanjana et al., "Improved vectors and genome-wide libraries for CRISPR screening," Nature Methods, Jul. 30, 2014, 11:783-784.

Shalem et al., "Genome-Scale CRISPR-Cas9 Knockout Screening in Human Cells," Science, Jan. 3, 2014, 343(6):84-87.

Tafesse et al., "GPR107, a G-protein-coupled Receptor Essential for Intoxication by Pseudomonas aeruginosa Exotoxin A, Localizes to the Golgi and Is Cleaved by Furin," Journal of Biological Chemistry, Aug. 2014, 289(35):24005-24018.

Vandenberghe et al., "Heparin binding directs activation of T cells against adeno-associated virus serotype 2 capsid," Nature Medicine, Jul. 16, 2006, 12:967-971.

Vandenberghe et al., "Presenter Disclosure," American Society of Gene & Cell Therapy, 13th Annual Meeting, Washington, DC, May 19-22, 2010, 15 pages.

Vinogradova et al., "Molecular mechanism of lysosomal sialidase deficiency in galactosialidosis involves its rapid degradation," Biochemical Journal, Mar. 1, 1998, 330(2):641-650.

Von Itzstein et al., "Rational design of potent sialidase-based inhibitors of influenza virus replication," Nature, Jun. 3, 1993, 363:418-423.

Walters et al., "Binding of Adeno-associated Virus Type 5 to 2,3-Linked Sialic Acid Is Required for Gene Transfer," Journal of Biological Chemistry, Jan. 2001, 276(23):20610-20616.

Xiao et al., "Engineering AAV for Improved In Vitro Infectivity, In Vivo Tropism and Onset of Expression, " Molecular Therapy, May 2010, 18:S1, 1 page.

Partial Supplementary European Search Report in European Appln. No. 19851371.5, dated May 19, 2022, 11 pages.

Extended European Search Report in European Appln. No. 19851371.5, dated Aug. 24, 2022, 10 pages.

Notice of Allowance in Japanese Appln. No. 2021-509223, dated Feb. 6, 2024, 5 pages (with English translation).

Office Action in Japanese Appln. No. 2021-509223, dated Jun. 27, 2023, 10 pages (with English translation).

\* cited by examiner

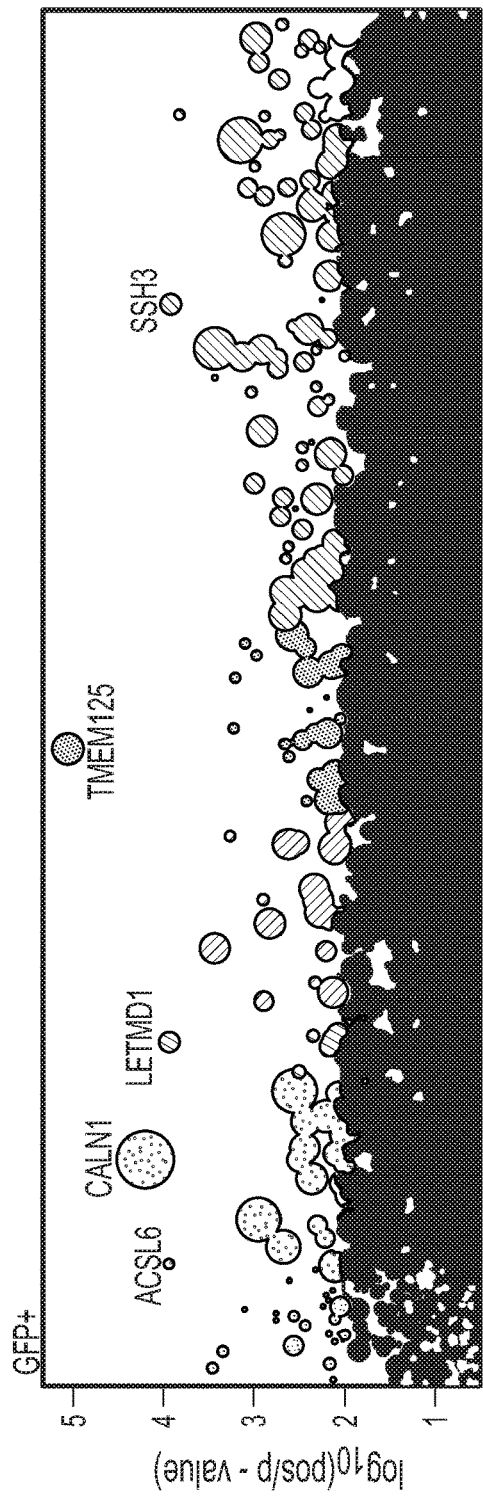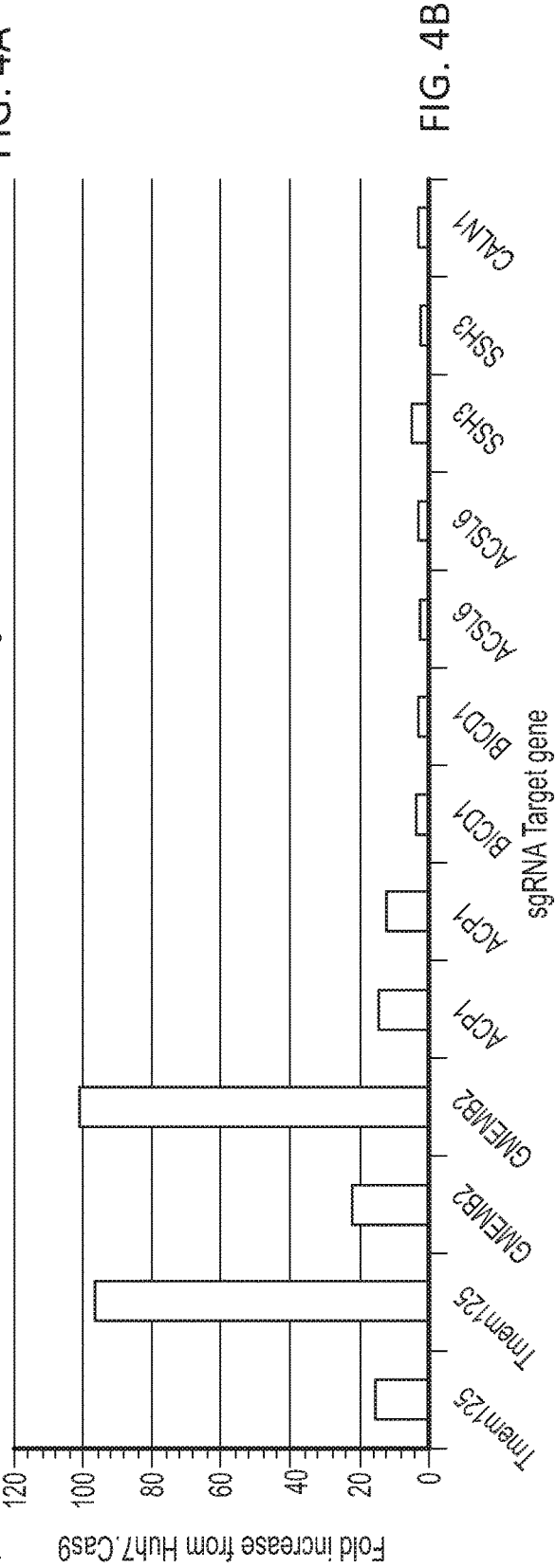
FIG. 4A
FIG. 4B

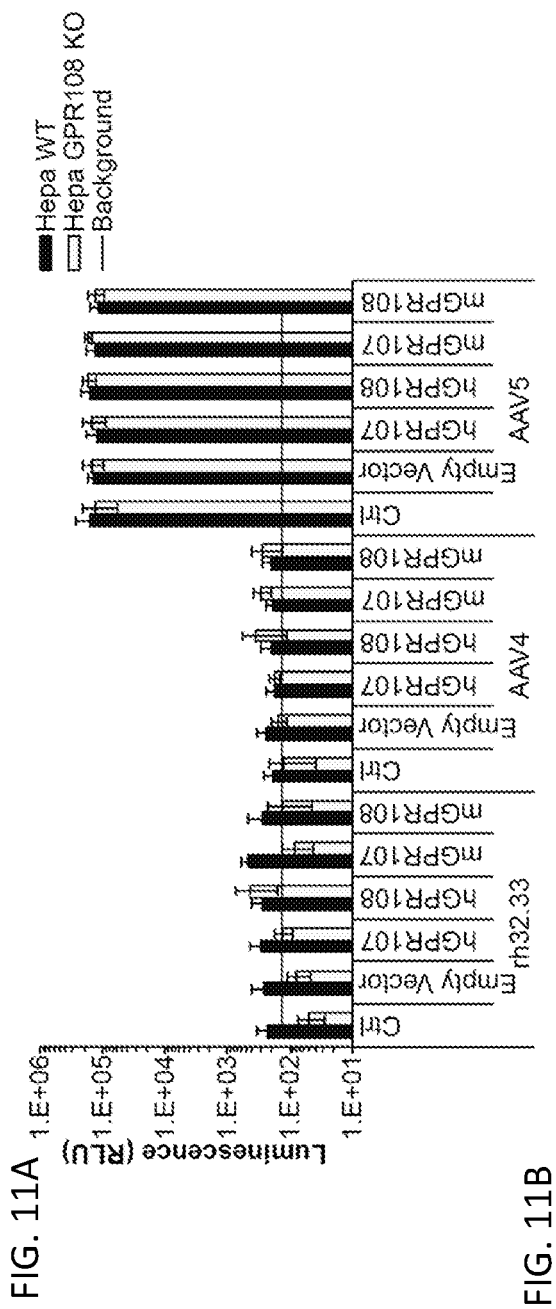
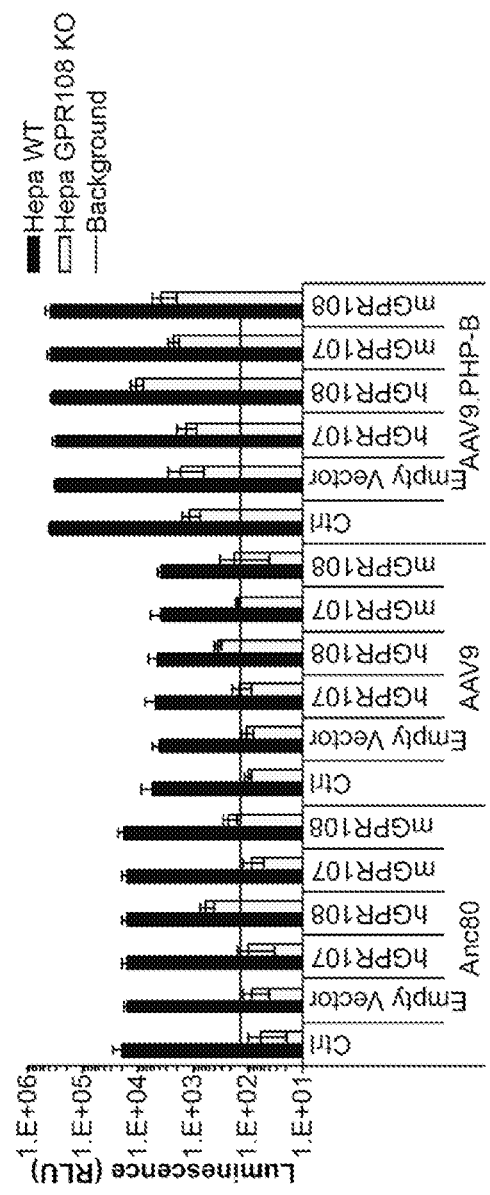
FIG. 11A
FIG. 11B

| | | | | |
|---|---|---|---|---|
| AAV5 | MSF|VDHPPDWLEE-VG|EGLREFLGLEA|GPPKPKPNQQHQDQARGLVL | 46 |
| AAV2 | MAADGYLPDWLEDTLSEGIRQ|WWKLKPGPPPPKPAERHKDDSRGLVL | 47 |
| AAV4 | -MTDGYLPDWLEDNLSEGVREWWALQPGAPKPKANQQHQDNARGLVL | 46 |
| AAVrh32.33 | MAADGYLPDWLEDNLSEGIREWWDLKPGAPKPKANQQKQDDGRGLVL | 47 |
| AAVanc80L65 | MAADGYLPDWLEDNLSEGIREWWDLKPGAPKPKANQQKQDDGRGLVL | 47 |
| AAV1 | MAADGYLPDWLEDNLSEGIREWWDLKPGAPKPKANQQKQDDGRGLVL | 47 |
| AAV6.2 | MAADGYLPDWLEDNLSEGIREWWDLKPGAPKPKANQQKQDDGRGLVL | 47 |
| AAV8 | MAADGYLPDWLEDNLSEGIREWWALKPGAPKPKANQQHQDNARGLVL | 47 |
| AAV3 | MAADGYLPDWLEDNLSEGIREWWALKPGVPQPKANQQHQDNRRGLVL | 47 |
| AAV9 | MAADGYLPDWLEDNLSEGIREWWALKPGAPQPKANQHQDNARGLVL | 47 |

FIG 16

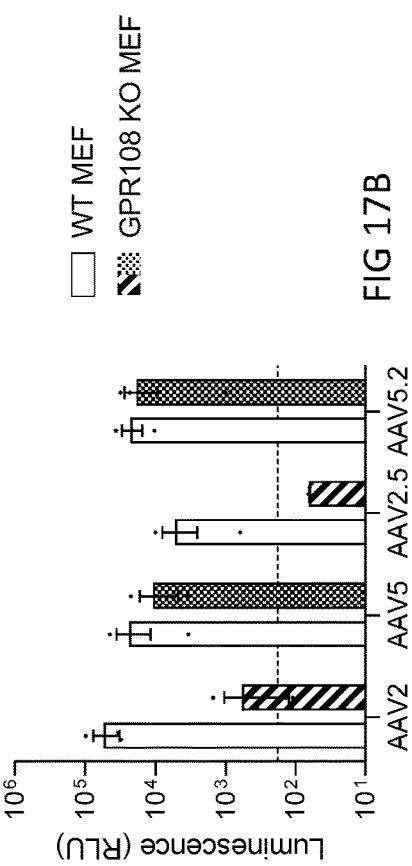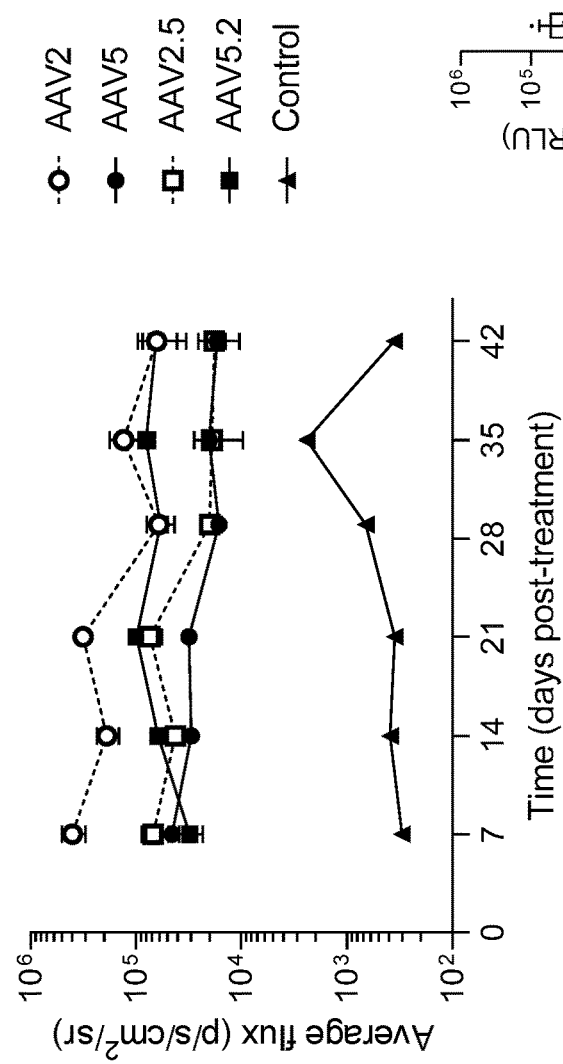
FIG 17A
FIG 17B

COMPOSITIONS AND METHODS FOR MODULATING TRANSDUCTION EFFICIENCY OF ADENO-ASSOCIATED VIRUSES

CROSS REFERENCE TO RELATED APPLICATIONS

The present application is the National Phase application of International Patent Application No. PCT/US2019/047546, filed on Aug. 21, 2019, which claims benefit to U.S. Application No. 62/720,859, filed on Aug. 21, 2018, the disclosures of which are incorporated herein by reference.

This application contains a Sequence Listing that has been submitted electronically as an ASCII text file named "SequenceListing.txt." The ASCII text file, created on Feb. 18, 2021, is 17,654 bytes in size. The material in the ASCII text file is hereby incorporated by reference in its entirety.

TECHNICAL FIELD

This disclosure generally relates to modified adeno-associated viruses (AAV) and methods of modulating the transduction efficiency of such viruses.

BACKGROUND

Previous methodologies have been insufficient to identify major AAV entry factors or to characterize subfamily-wide receptor and entry factor requirements. Previous studies have primarily focused on cDNA overexpression in poorly permissive cell lines to identify factors that increase transduction of a particular serotype (76, 80, 81), most often AAV2 (74, 75, 77). These studies have identified several proteins that increase AAV transduction, yet the mechanism by which they influence transduction has been poorly characterized aside from often demonstrating increased attachment at the cell surface upon overexpression (78). There is a disconnect in the data however, as knock-down and knock-out studies of these factors often do not show a major defect in AAV transduction, and thus cannot be defined as a required entry receptor.

SUMMARY

The present disclosure relates to the mechanism by which adeno-associated virus (AAV) transduces cells. Having an understanding of this mechanism allows a person of skill in the art to modulate the entry and, hence, the transduction efficiency, of AAVs into cells.

As described herein, methods of modulating the transduction efficiency of an adeno-associated virus (AAV) into a cell are provided. Such methods typically include introducing a genetically-modified adeno-associated virus (AAV) into the cell, where the AAV capsid has been genetically modified to comprise a heterologous VP1 polypeptide sequence and where the heterologous VP1 polypeptide sequence requires the presence of a GPR108 receptor for transduction or does not require the presence of a GPR108 receptor for transduction of the cell.

In some embodiments, the heterologous VP1 polypeptide or portion thereof includes the sequence shown in SEQ ID NO:1. In these instances, the heterologous VP1 polypeptide sequence does not require the presence of a GPR108 receptor for transduction of the cell. One example of a VP1 polypeptide that includes the sequence shown in SEQ ID NO:1 is the amino acid sequence of an AAV5 VP1 protein or a portion thereof.

In some embodiments, the heterologous VP1 polypeptide or portion thereof includes the sequence shown in SEQ ID NO:2. In these instances, the heterologous VP1 polypeptide sequence requires the presence of a GPR108 receptor for transduction. Examples of VP1 polypeptide that includes the sequence shown in SEQ ID NO:2 are the amino acid sequences of a VP1 protein or a portion thereof from AAV1, AAV2, AAV3, AAV4, AAV6.2, AAV7, AAV8, AAV9, Anc80, Anc81, Anc82, Anc83, Anc84, Anc110, Anc113, rh8c, rh10, PHP-B, 8BPV2, or 7M8.

Also as described herein, methods of modifying the cell entry of an adeno-associated virus (AAV) are provided. Such methods typically include genetically engineering an AAV to be GPR108-independent, where the genetically engineered GPR108-independent AAV includes a VP1 polypeptide sequence having the sequence $MX_1X_2VDHPX_3X_4X_5X_6X_7EVGX_8X_9X_{10}X_{11}X_{12}FLGLEA$ (SEQ ID NO:1), wherein each of $X_{1-12}$ is any amino acid. Alternatively, such methods can include genetically engineering an AAV to be GPR108-dependent, where the genetically engineered GPR108-dependent AAV includes a VP1 polypeptide sequence having the sequence $MX_1X_2DGYLX_3X_4X_5X_6X_7D(T/N)LSX_8X_9X_{10}X_{11}X_{12}WW(K/A/D)L(K/Q)P$ (SEQ ID NO:2), wherein each of $X_{1-12}$ is any amino acid, thereby modifying the cell tropism of the AAV.

An exemplary genetically engineered GPR108-dependent AAV includes a VP1 polypeptide sequence having the sequence $MX_1X_2VDHPX_3X_4X_5X_6X_7EVGX_8X_9X_{10}X_{11}X_{12}FLGLEA$ (SEQ ID NO:1), wherein $X_1$ is S or A or T; $X_2$ F or A or T; $X_3$ is P; $X_4$ is D; $X_5$ is W; $X_6$ is L; $X_7$ is E; $X_8$ is E; $X_9$ is G; $X_{10}$ is L or I or V; $X_{11}$ is R; and/or $X_{12}$ is E or Q. In one embodiment, the genetically engineering GPR108-independent AAV includes a VP1 polypeptide sequence derived from an AAV5 VP1 protein.

Similarly, an exemplary genetically engineered GPR108-dependent AAV includes a VP1 polypeptide sequence having the sequence $MX_1X_2DGYLX_3X_4X_5X_6X_7D(T/N)LSX_8X_9X_{10}X_{11}X_{12}WW(K/A/D)L(K/Q)P$ (SEQ ID NO:2), wherein $X_1$ is S or A or T; $X_2$ is F or A or T; $X_3$ is P; $X_4$ is D; $X_5$ is W; $X_6$ is L; $X_7$ is E; $X_8$ is E; $X_9$ is G; $X_{10}$ is L or I or V; $V_{11}$ is R; and/or $X_{12}$ as E or Q. In some embodiments, the genetically engineering GPR108-dependent AAV comprises a VP1 polypeptide sequence derived from a VP1 protein of AAV 1, AAV2, AAV3, AAV4, AAV6.2, AAV7, AAV8, AAV9, Anc80, Anc81, Anc82, Anc83, Anc84, Anc110, Anc113, rh8c, rh10, PHP-B, 8BPV2, or 7M8.

In addition, methods of increasing the transduction efficiency of an adeno-associated virus (AAV) into a cell are provided. Such methods typically include contacting the cell with a compound that increases the expression or activity of GPR108 in the cell, thereby increasing the transduction efficiency of the AAV into the cell.

A representative compound that can be used to increase the expression of GPR108 in the cell, is an expression construct including a GPR108 transgene. In some embodiments, the AAV is AAV1, AAV2, AAV3, AAV4, AAV6.2, AAV7, AAV8, AAV9, Anc80, Anc81, Anc82, Anc83, Anc84, Anc110, Anc113, rh8c, rh10, PHP-B, 8BPV2, or 7M8. In some embodiments, the AAV is a genetically-engineered AAV.

Also as described herein, methods of decreasing the transduction efficiency of an adeno-associated virus (AAV) into a cell are provided. Such methods typically include contacting the cell with a compound that decreases the expression or activity of GPR108 in the cell, thereby decreasing, the transduction efficiency of the AAV into the cell.

A representative compound that can be used to decrease the expression of GPR108 in the cell is an interfering RNA molecule. In some embodiments, the interfering RNA molecule is siRNA or RNAi.

The cells used in any of the methods described herein can be in vivo. Representative cells include liver cells, kidney cells, heart cells, lung cells, epithelial cells, endothelial cells, bone marrow cells (including hematopoietic stem cells).

In addition, methods of increasing the uptake of a therapeutic agent into a cell are provided. Such methods typically include contacting the cell with the therapeutic agent linked to an AAV VP1 polypeptide, where the VP1 polypeptide includes the sequence $MX_1X_2VDHPX_3X_4X_5X_6X_7X_8X_9X_{10}X_{11}X_{12}FLGLEA$ (SEQ ID NO:1), wherein each of $X_{1-12}$ is any amino acid.

Representative therapeutic agents include proteins or protein complexes. In some embodiments, the therapeutic agent is further linked to a binding factor that binds to GPR108. Representative binding factors that bind to GPR108 include, without limitation, an antibody, an aptamer, and an antibody domain.

Further, compositions including a therapeutic agent linked to a VP1 polypeptide comprising SEQ ID NO:1 or SEQ ID NO:2 are provided. In some embodiments, the therapeutic agent is a protein or protein complex.

In addition, AAV capsid sequences are provided that include a heterologous VP1 sequence that includes SEQ ID NO:2. A representative heterologous VP1 sequence includes the sequence shown in SEQ ID NO:18.

AAV capsid sequences also are provided that include a heterologous VP1 sequence that includes SEQ ID NO:2. A representative heterologous VP1 sequence includes the sequence shown in SEQ ID NO:19.

In one aspect, the disclosure provides methods of modulating the transduction efficiency of an adeno-associated virus ((AAV)) into a cell. Such methods include introducing a genetically-modified adeno-associated virus (AAV) into the cell, where the AAV capsid has been genetically modified to comprise a heterologous VP1 polypeptide or portion thereof, and where the heterologous VP1 polypeptide or portion thereof is involved in GPR108-dependent or GPR108-independent transduction of the cell, depending on the sequence of the VP1 polypeptide. In some embodiments, the heterologous VP1 polypeptide or portion thereof is a VP1 polypeptide or portion thereof from AAV5, in which case the AAV is GPR108-independent. In some embodiments, the genetically modified AAV is an AAV that is AAV Receptor (AAVR)-independent.

In another aspect, the disclosure features methods of modulating the uptake of a non-AAV compound into a cell. Such methods include contacting the cell with the non-AAV compound linked to a GPR108-dependent AAV VP1 polypeptide or portion thereof. In some embodiments, the non-AAV compound is a protein or protein complex. In some embodiments, the GPR108-dependent AAV VP1 polypeptide or portion thereof originates from AAV1, AAV2, AAV3, AAV4, AAV6.2, AAV7, AAV8, AAV9, Anc80, Anc81, Anc82, Anc83, Anc84, Anc110, Anc113, rh8c, rh10, PHP-B, 8BPV2, and 7M8. In some embodiments, the non-AAV compound is further linked to a binding factor that binds GPR108. Representative binding factors that bind GPR108 include, without limitation, an antibody, an aptamer, and an antibody domain.

In still another aspect, the disclosure features methods of increasing the transduction efficiency of an adeno-associated virus (AAV) into a cell. Such methods include contacting the cell with a compound, that increases the expression or activity of GPR108 in the cell, thereby increasing the transduction efficiency of the AAV into the cell. In some embodiments, the compound that increases the expression of GPR108 in the cell is an expression construct comprising a GPR108 transgene.

In yet another aspect, the disclosure provides methods of decreasing the transduction efficiency of an adeno-associated virus (AAV) into a cell. Such methods include contacting the cell with a compound that decreases the expression or activity of GPR108 in the cell, thereby decreasing the transduction efficiency of the AAV into the cell. In some embodiments, the compound that decreases the expression of GPR108 in the cell is an interfering RNA molecule. Representative interfering RNA molecules include, without limitation, siRNA and RNAi. In some embodiments, the compound that decreases the activity of GPR108 in the cell is an antibody that specifically binds to GPR108 (i.e., an anti-GPR108 antibody).

The cells in any of the methods described herein can be in vivo cells. Representative cells include, without limitation, liver cells, kidney cells, heart cells, lung cells, epithelial cells, endothelial cells, bone marrow cells (including hematopoietic stem cells).

This disclosure enables the creation of novel capsids with unique cell and tissue targeting properties, which can be used to target novel tissue or cell types not previously accessible to the AAV serotypes in current use. Specifically, the methods and compositions described here allow for AAV vectors to be altered to either engage a cellular receptor, GPR108, or lose dependency on the use, and need for GPR108, leading to AAV vectors to either gain access to GPR108-expressing cells or not be restricted by GPR108 expression in the target cell type.

As used herein, transduction efficiency refers to the proportion of a plurality of viruses that are able to gain entry and infect a cell.

As used herein, "derived" in the context of a VP1 polypeptide sequence refers to the serotype from which the VP1 polypeptide sequence arose or originated. The VP1 polypeptide can be expressed, generated, or synthesized in any manner.

A genetically-engineered virus refers to a virus in which a nucleic acid sequence has been changed. Methods of genetically engineering viruses are known in the art and are discussed further herein.

A "heterologous" polypeptide or portion thereof refers to a polypeptide or a portion thereof that is not native to the rest of the polypeptide or to the organism in which the heterologous polypeptide resides.

A "GPR108-dependent" AAV refers to an AAV that requires the presence of GPR108 for transduction into a cell. On the other hand, a GPR108-independent AAV refers to an AAV that does not require the presence of GPR108 for transduction into a cell.

A "VP1 protein" is typically a VP1 protein or a portion thereof from a particular AAV serotype exhibiting either GPR108-independence or GPR108-dependence. A "VP1 polypeptide" is a molecule derived from a VP1 protein or a portion thereof that is incorporated into the capsid of an AAV to impart a GPR108 dependence to the AAV. As described herein, the GPR108 dependence imparted to the AAV by the VP1 polypeptide is usually different compared to the GPR108 dependence of the wild type VP1 protein normally found in that AAV. A representative GPR108-independent sequence is MX$_1$X$_2$VDHPX$_3$X$_4$X$_5$X$_6$X$_7$EVG X$_8$X$_9$X$_{10}$X$_{11}$X$_{12}$FLGLEA (SEQ ID NO:1, wherein each of X$_{1-12}$ can be any amino acid), while a representative GPR108-dependent sequence is MX$_1$X$_2$DGYLX$_3$X$_4$X$_5$X$_6$X$_7$D(T/N)LSX$_8$X$_9$X$_{10}$X$_{11}$X$_{12}$WW(K/A/D)L(K/Q)P (SEQ ID NO:2, wherein each of X$_{1-12}$ can be any amino acid).

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 4A is the Robust Rank Aggregation (RRA) analysis to identify genes enriched in cells highly expressing GFP, suggestive of potential AAV restriction factors.

FIG. 4B is a bar graph showing the fold increase in transduction of rh32.33.CMV.Luciferase.SVPA into CRISPR-edited polyclonal cell populations generated by transducing Huh7 AAVR KO Cas9 cells with lentivirus encoding sgRNAs targeting individual genes identified in rh32.33 GRP+ cell population.

FIGS. 11A-11B are graphs of the luminescence observed in Hepa WT or GPR108 KO cells transfected with flag-tagged human or mouse GPR107 or GPR108 and transduced with rh32.33, AAV4, AAV5, (11A) and Anc80, AAV9, and AAV9.PHP-B (11B) expressing a luciferase-encoding transgene.

FIG. 16 is an alignment of the region known to confer GPR108 dependency (AAV5 (SEQ ID NO:8); AAV2 (SEQ ID NO:9); AAV4 (SEQ ID NO:10); AAVrh32.33 (SEQ ID NO:11); AAVanc80L65 (SEQ ID NO:12); AAV1 (SEQ ID NO:13); AAV6.2 (SEQ. ID NO:14); AAV8 (SEQ ID NO:15); AAV3 (SEQ ID NO:16); and AAV9 (SEQ ID NO:17)).

FIG. 17A is a graph of in vivo luciferase expression (p/s/cm2/sr) during 6-week follow-up of C57BL/6J mice treated with 1e11gc/mouse of version 1 of cap 2-5 chimeras in AAV2, AAV5, AAV2.5, AAV5.2 or PBS (control). Data is shown as mean±SEM of 5 animals per group.

FIG. 17B is a graph of luciferase (RLU/s) in wild type MEF or GPR108 KO MEF transduced with the indicated AAV expressing a luciferase transgene 48 h after transduction. Data are shown as mean±SEM of three independent experiments.

DETAILED DESCRIPTION

The work described in this disclosure is one of the first instances of a highly stringent genome-wide screen to identify viral entry factors being used to understand the entry pathway of a gene therapy vector. Three novel host cell entry factors are identified and characterized, and test results for both AAVR-independent and AAVR-dependent AAV serotypes are described. The highly conserved usage of two entry factors, AAVR and G protein-coupled receptor 108 (GPR108), demonstrate that most AAVs appear to share the same entry pathway. A novel multi-factor entry mechanism is presented in which most AAVs bind and require AAVR for proper trafficking, followed by a requirement of GPR108 for endosomal escape (FIG. 1).

Figure 1:
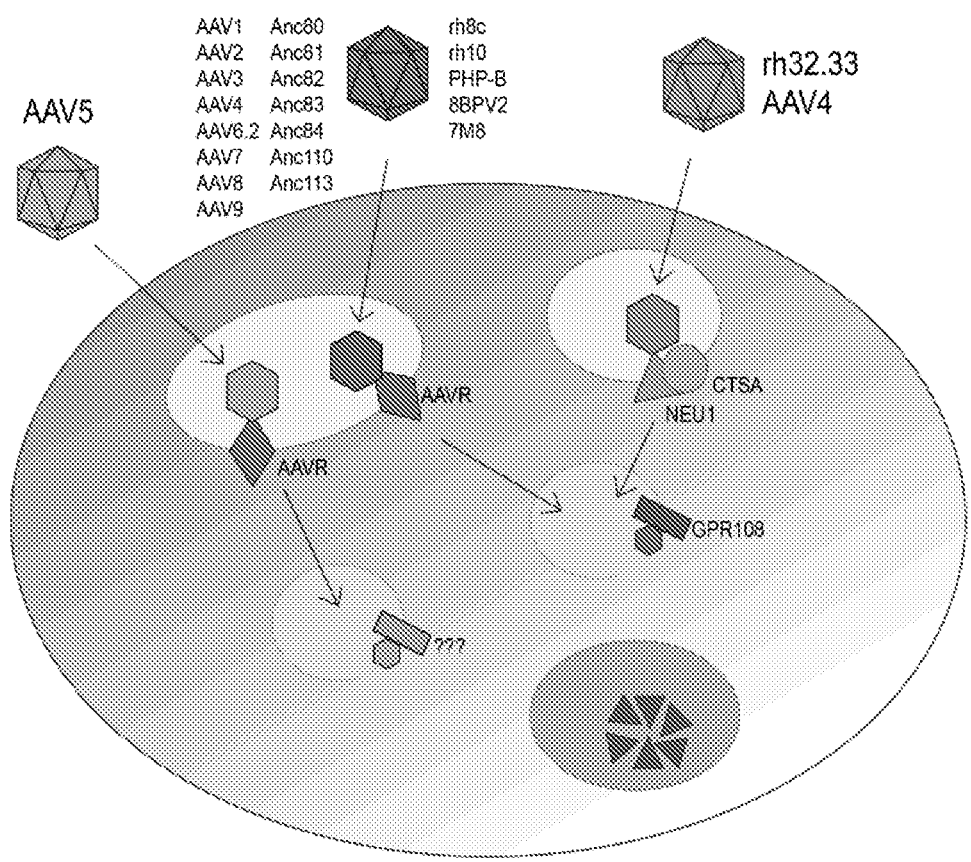
FIG. 1 is model of the usage of AAV cellular entry receptors, by serotype.

FIG. 1 is a schematic of a model, based on the work described herein, of AAV cellular entry receptors. For example, most AAV serotypes (e.g., AAV1, AAV2, AAV3, AAV4, AAV6.2, AAV7, AAV8, AAV9, Anc80, Anc81, Anc82, Anc83, Anc84, Anc110, Anc113, rh8c, rh10, PHP-B, 8BPV2, and 7M8) require both AAVR and GPR108 for cellular entry (e.g., in both human and mouse); both AAVR and GPR108 are reported to be ubiquitously expressed. On the other hand, AAV5 uniquely uses an alternate domain of AAVR, and not GPR108, as well as a currently unknown co-receptor for endosomal escape, and AAV4 and rh32.33 use a minimal receptor complex of neuraminidase 1 (NEU1) and cathepsin A (CTSA), as well as the GPR108 receptor for endosomal escape.

As described herein, the AAV sequences involved in cellular entry can be engineered to produce novel capsids with unique cell and tissue targeting properties, allowing targeting of specific tissues or cell types not previously accessible to the current AAV serotypes. AAV, like any virus, engages host proteins and other co-factors for entry and several other steps that allow for a productive infection. Here, we describe a generalizable method that allows AAV vectors to be modified to depend on GPR108, thereby allowing access to GPR108-expressing cells and tissues, or conversely, to be relieved of GPR108 dependency, thereby allowing vectors not to be restricted by the need for GPR108 expression in the target cell. In addition, based on the mechanism of entry described herein, the transduction efficiency of AAV into cells can be modulated or altered using a number of different methods. For example, the methods described herein can be used to modify the cell entry of an adeno-associated virus (AAV).

The ability to manipulate or control, at least in part, the entry of an AAV into a cell has far-reaching therapeutic implications. AAVs can be used therapeutically to treat a large number of different diseases or deficiencies, and the methods described herein can be used to modulate the transduction efficiency of one or more cells by those AAVs. For example, AAVs can be used to deliver therapy (e.g., gene therapy) to cells for the treatment of a wide variety of disorders including hemophilia, retinitis pigmentosa, cystic fibrosis, leber congenital amaurosis, lysosomal storage disorders, inborn errors of metabolism (e.g., inborn errors of amino acid metabolism including phenylketonuria, inborn errors of organic acid metabolism including propionic academia, inborn errors of fatty acid metabolism including medium-chain acyl-CoA dehydrogenase deficiency (MCAD)), cancer, achromatopsia, cone-rod dystrophies, macular degenerations (e.g., age-related macular degeneration), lipopolypeptide lipase deficiency, familial hypercholesterolemia, spinal muscular atrophy, Duchenne's muscular dystrophy, Alzheimer's disease, Parkinson's disease, obesity, inflammatory bowel disorder, diabetes, congestive heart failure, hypercholesterolemia, hearing loss, coronary heart disease, familial renal amyloidosis, Marfan's syndrome, fatal familial insomnia, Creutzfeldt-Jakob disease, sickle-cell disease, Huntington's disease, fronto-temporal lobar degeneration, Usher syndrome, lactose intolerance, lipid storage disorders (e.g., Niemann-Pick disease, type C), Batten disease, choroideremia, glycogen storage disease type II (Pompe disease), ataxia telangiectasia (Louis-Bar syndrome), congenital hypothyroidism, severe combined immunodeficiency (SCID), and/or amyotrophic lateral sclerosis (ALS).

Genetically Engineered Adeno-Associated Viruses (AAVs)

As described herein, the transduction efficiency of an adeno-associated virus (AAV) into a cell can be modulated or altered by generating a non-naturally occurring, genetically modified adeno-associated virus (AAV) and introducing a plurality of the genetically modified AAVs into the cell.

A VP1 polypeptide or portion thereof refers to the VP1 unique N-terminal portion within the AAV sequence. VP1, VP2, and VP3 are overlapping C-terminal proteins, which result in a VP12 unique domain at the N terminus of VP1 and VP2 (referred to as "VP12u") and a unique VP1 domain (referred to as "VP1u"). As demonstrated herein, GPR108 engagement has been mapped to the VP1u domain.

As described herein, the AAV capsid protein can be genetically engineered to include a heterologous VP1 polypeptide sequence that imparts a requirement for the presence of a GPR108 receptor for transduction of a cell to an AAV that otherwise, in a non-genetically engineered form, does not require the presence of as GPR108 receptor for transduction of the cell. Alternatively, the AAV capsid protein can be genetically engineered to include a heterologous VP1 polypeptide sequence that removes the requirement for the GPR108 receptor for transduction of a cell to an AAV that otherwise, in a non-genetically engineered form, requires the presence of a GPR108 receptor for transduction of the cell.

For example, an AAV can be genetically engineered to include a VP1 sequence having the sequence $MX_1X_2VDHPX_3X_4X_5X_6X_7EVGX_8X_9X_{10}X_{11}X_{12}FLGLEA$ (SEQ ID NO:1, wherein the $X_S$ can be any amino acid), which imparts GPR108-independence to the AAV (e.g., removing the requirement for GPR108). In some embodiments, $X_1$ ran be S or A or T; $X_2$ can be F or A or T; $X_3$ can be P; $X_4$ can be D; $X_5$ can be W; $X_6$ can be L; $X_7$ can be E; $X_8$ can be E; $X_9$ can be G; $X_{10}$ can be L or I or V; $X_{11}$ can be R; and/or $X_{12}$ can be E or Q.

A representative GPR108-independent VF1 sequence is MAAVDHPPDWLEEVGEGIREFLGLEA (SEQ ID NO:18).

Alternatively, an AAV can be genetically engineering to include a VP1 sequence having the sequence $MX_1X_2DGYLX_3X_4X_5X_6X_7D(T/N)LSX_8X_9X_{10}X_{11}X_{12}WW(K/A/D)L(K/Q)P$ (SEQ ID NO:2, wherein the Xs can be any amino acid), which imparts GPR108-dependence to the AAV (e.g., requiring the presence of GPR108). In some embodiments, $X_1$ can be S or A or T; $X_2$ can be F or A or T; $X_3$ can be P; $X_4$ can be D; $X_5$ can be W; $X_6$ can be L; $X_7$ can be E; $X_8$ can be E; $X_9$ can be G; $X_{10}$ can be L or I or V; $X_{11}$ can be R; and/or $X_{12}$ can be E or Q.

A representative GPR108-dependent VP1 sequence is

```
                                            (SEQ ID NO: 19)
MSFDGYLPDWLEDTLSEGLREWWKLKP
```

In other embodiments, SEQ ID NO:8 (shown in FIG. 16, and which is a portion of the VP1 sequence from AAV5) is an example of a GPR108-independent sequence, while SEQ ID NOs: 9-17 (shown in FIG. 16 and each corresponding to a portion of the VP1 sequence from AAV2, AAV4, rh32.33, AAVanc80L65, AAV1, AAV6.2, AAV8, AAV3, and AAV9, respectively) are examples of GPR108-dependent sequences, although it would be appreciated that VP1 sequences other than those shown here can impart GPR108-independence or GPR108-dependence. For example, a homologous VP1 polypeptide (e.g., the corresponding portion of the VP1 protein) from AAV7, Anc81, Anc82, Anc83, Anc84, Anc110, Anc113, rh8c, rh10, PHP-B, 8BPV2, or 7M8 also can impart GPR108-dependence.

As described herein, the VP1 polypeptide is involved in either GPR108-dependent or GPR108-independent transduction of a cell, depending on the VP1 protein of ran AAV serotype from which the VP1 polypeptide was derived. Therefore, an AAV can be genetically engineered to include a heterologous VP1 polypeptide to modify the cell entry and ultimate transduction efficiency of the genetically engineered AAV.

For example, a normally GPR108-dependent AAV can be genetically modified to include a heterologous VP1 polypeptide that will cause an AAV to exhibit GPR108-independent transduction into cells, or a normally GPR108-independent AAV can be genetically modified to include a heterologous VP1 polypeptide that causes the AAV exhibit GPR108-dependent transduction into cells.

In some instances, the heterologous VP1 polypeptide is derived from a VP1 protein or portion thereof from AAV5. As demonstrated herein, the AAV5-derived VP1 polypeptide can impart GPR108-independence to an otherwise GPR108-dependent AAV. In some instances, the AAV that is genetically modified to include a heterologous VP1 polypeptide is AAV that is AAV Receptor (AAVR)-independent. AAVR-independent AAVs are known in the art and include, for example, AAV4 and rh32.33. For example, AAVR-independent AAV can be genetically-engineered to also be GPR108-independent using the methods described herein.

Methods of Modulating the Transduction Efficiency of AAV

Based on the understanding of, the AAV cellular entry mechanism provided by this disclosure, it may be desirable, in some instances, to increase the transduction efficiency of an adeno-associated virus (AAV) into a cell by increasing the expression or activity of GPR108 in the cell. Similarly, based on the understanding of the AAV cellular entry mechanism provided by this disclosure, it may be desirable, in some instances, to decrease the transduction efficiency of an adeno-associated virus (AAV) into a cell by contacting the cell with a compound that decreases the expression or activity of GPR108 in the cell.

Methods of increasing the expression or activity of a protein in a cell are generally known and typically include, for example, introducing an expression construct into the cells, where the expression construct expresses, or overexpresses, a transgene encoding the desired protein (e.g., a GPR108 transgene). Similarly, methods of decreasing the expression or activity of a protein are generally known and typically include, for example, expressing an interfering RNA in the cell. Interfering RNAs are known in the art and include, without limitation, small interfering RNAs (siRNAs) and RNA interference (RNAi) molecules.

Human GPR108 sequences as well as mouse and rat GPR108 sequences are known in the art. See, for example, NM_001080452 (human GPR108 transcript variant 1); NM_020171 (human GPR108 transcript variant 2) NP_001073921 (human GPR108 protein isoform 1); AF:376726 (mouse GPR108 transcript); and BC061996 (rat GPR108 transcript). Such sequences can be used to generate an expression construct for expressing a GPR108 transgene, or such sequences can be used to generate one or more interfering RNAs. A representative interfering RNA sequence toward GPR108 has the sequence of CGC ACA AGC CCA UUU GGA A (SEQ ID NO:20) (designated siRNA3 in Kaur, 2018, PhD. Thesis for National University of Singapore; available at scholarbank.nus.edu.sg/handle/10635/142828 on the World Wide Web).

Expression constructs are known in the art and are commercially available or can be produced by recombinant DNA techniques routine in the art. Expression constructs typically include one or more regulatory elements operably linked to transgene, and further can include sequences such as those encoding a selectable marker (e.g., an antibiotic resistance gene). A construct designed to express a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST))

Regulatory elements include nucleic acid sequences that direct and regulate expression of nucleic acid coding sequences. One example of a regulatory element is a promoter sequence. Regulatory elements also can include introns, enhancer sequences, response elements, or inducible elements that modulate expression of a nucleic acid (e.g., a transgene). Regulatory elements can be of bacterial, yeast, insect, mammalian, or viral origin and constructs can contain a combination of regulatory elements from different origins. As used herein, operably linked means that elements for expression are positioned in a construct relative to a coding sequence (e.g., a transgene) in such a way a to direct or regulate expression of the coding sequence. In some instances, operably linked means in-frame.

Constructs as described herein can be introduced into a host cell. As used herein, "host cell" refers to the particular cell into which the nucleic acid is introduced and also includes the progeny or potential progeny of such a cell. A host cell can be any prokaryotic or eukaryotic cell. For example, nucleic acids can be expressed in'bacterial cells such as *E. coli*, or in insect cells, yeast or mammalian cells (such as Chinese hamster ovary cells (CHO) or COS cells). Other suitable host cells are known to those skilled in the art.

The cells that are contacted as described herein (e.g., with a compound that increases or decreases the expression or activity of GPR108 or with a genetically modified AAV) can be cells cultured in vitro or cells in vivo, e.g., in a portion of tissue in an animal model or in a human or animal subject. Representative cell types include, without limitation, liver cells, kidney cells, heart cells, muscle cells, brain cells, lung cells, epithelial cells, endothelial cells, and bone marrow cells (including hematopoietic stem cells) or cells in the eye or inner ear. The cells that are contacted as described herein can be, for example, tumor cells or engineered cells.

Many methods for introducing nucleic acids into host cells, both in vivo and in vitro, are known to those skilled in the art and include, without limitation, electroporation, calcium phosphate precipitation, polyethylene glycol (PEG) transformation, heat shock, lipofection, microinjection, and viral-mediated nucleic acid transfer.

Delivery of Therapeutic Agents

The methods and, compositions described herein also can be used to modulate the uptake of a therapeutic agent into a cell. For example, a therapeutic agent such as a protein (e.g., an antibody, e.g., a monoclonal antibody) or a protein complex can be linked to a GPR108-dependent AAV VP1 polypeptide or portion thereof. In this manner, a therapeutic agent can be engineered to utilize the GPR108 uptake mechanism usually used by AAVs. Based on the disclosure herein, it would be understood that the GPR108-dependent AAV VP1 polypeptide can include the consensus sequence shown in SEQ ID NO:2 or the GPR108-dependent AAV VP1 polypeptide can be derived from the VP1 protein or portion thereof from any AAV that requires GPR108 for uptake (e.g., AAV1, AAV2, AAV3, AAV4, AAV6.2, AAV7, AAV8, AAV9, Anc80, Anc81, Anc82, Anc83, Anc84, Anc110, Anc113, rh8c, rh10, PHP-B, 8BPV2, of 7M8).

In some instances, it may be desirable to further link an additional binding factor to the therapeutic agent that has affinity to GPR108. Such a binding factor can be any molecule or agent that binds to GPR108 including, without limitation, an antibody, an antibody domain, or an aptamer. For example, the N-terminus of a therapeutic agent can be linked to a VP1 polypeptide that includes the consensus sequence, $MX_1X_2DGYLX_3X_4X_5X_6X_7D(T/N)LSX_8X_9X_{10}X_{11}X_{12}WW(K/A/D)L(K/Q)P$ (SEQ ID NO:2), to allow delivery of a therapeutic agent to cells.

In accordance with the present disclosure, there may be employed conventional molecular biology, microbiology, biochemical, and recombinant DNA techniques within the skill of the art. Such techniques are explained fully in the literature. The disclosure will be further described in the following examples, which do not limit the scope of the methods and compositions of matter described in the claims.

EXAMPLES

Materials and Methods

All cell lines were maintained in Dulbecco's modified Eagle's minimal medium DMEM (Corning) supplemented with 10% FBS (GE Healthcare) and 100 IU/mL penicillin/streptomycin (Corning) in a humidified incubator with 5% $CO_2$ at 37° C. All cell lines were a gift from Jan Carrette lab and were previously published (Pillay et al., 2016, Nature, 530:108-12). Cells were transfected using PolyJet In Vitro DNA Transfection Reagent (SignaGen, Cat#SL100688) using the standard protocol.

Primary cell MEFs were cultured ire Iscove Modified Dulbecco Media IMDM (Gibco) supplemented with 10% FBS (GE Healthcare), 55 µM beta-mercaptoethanol (Gibco), 15 µg/mL gentamicin sulfate (Thermo Fisher) and non-essential amino acids (Thermo Fisher). WT and GPR108 KO MEFs were a gift from Brian Seed and Guoling Zhou and were previously described (Dong et al., 2018, Plos One, 13(10):e0205303).

NCBI sequences used for synthesis were as follows: mouse GPR107, BAC 26961; mouse GPR108, NP_084360; human GPR107, AAK57695; human GPR108, XP_290854. Capsid chimeras were generated from AAV2 and AA5 nucleotide sequence at the VP1 junction demonstrated in (Excoffon et al., 2009, PNAS USA, 106:3865-70). Capsid chimeras were synthesized by Genewiz and subcloned into pAAVector2 using HindIII and SpeI restriction sites.

High titer vectors were produced, purified, and titrated by the MEEI/SERI Gene Transfer Vector Core (vector.meei-.harvard.edu on the World Wide Web). Large scale vector preparations were generated by polyethyleniminc (Poly-sciences, Cat#24765-2) triple transfection of pHelp, pAAVector2[Cap], and pCMV.Luciferase.SVPA, pCMV.eGFP.T2.A.Luciferase, or pCMV.eGFP.WPRE.bGH transgenes in a 2:1:1 ratio. 520 µg total DNA was transfected in ten-layer hyperflasks using a PEI Max:DNA ratio of 1.375:1 (w/w). Three days after transfection, vectors were concentrated by tangential flow filtration and purified by iodixanol gradient ultracentrifugation as previously described (Lock et al., 2010, Hum. Gene Ther., 21:1259-71).

Chimeric and point mutant viral vectors were produced on a smaller scale as crude viral preparations by same transfection method in 10 cm cell culture plates. Three days after transfection, cells and supernatant were collected, subjected to three freeze-thaw cycles, then crude virus preparation was clarified by centrifugation for 10 min at 10,000 RPM in a ThermoScientific FIBERLite F15-8×50cy rotor at 4° C.

All luciferase transduction assays were done by seeding 10,000 cells per well in black-bottom 96 well plates overnight. When indicated, cells were pre-incubated with 200 pfu/cell of WT hAd5 (University of Pennsylvania Vector core) in D10 for two hours, then hAd5-containing medium was removed prior to transduction. Cells were transduced with either AAV at $1\times10^4$ VG/cell in 50 µL serum-free DMEM (AAVR rescue experiments) for 1 h at 37° C., then D10 was added to a total volume of 200 µL, or 100 µl per well of crude virus prep (chimeric, and point mutant capsid experiments) was added for 1 h at 37° C., removed, then D10 was added. Transduction levels were analyzed by luciferase assay 48 hours post-transduction.

Two days post-transduction, cell culture medium was removed and cells were lysed in 20 µL per well of 1× Reporter Lysis Buffer (Promega, Cat#), then frozen at −80° C. After thaw, ffLuc expression was measured in Relative Light Units/s on a Synergy H1 Hybrid Multi-Mode Microplate reader using 100 µL luciferin buffer [200 mM Tris pH 8, 10 mM $MgCl_2$, 300 µM ATP, 1× Firefly Luciferase signal enhancer (Thermo Cat#16180), and 150 µg/mL D-Luciferin].

Example 1

Entry Screen and Analysis

Lentivirus was produced from HEK293T cells (ATCC, Manassas, VA), by transient transfection using PolyJet In Vitro DNA Transfection Reagent (SignaGen, Cat#SL100688) using manufacturer's, protocol for lentiviral production. LentiCas9-blast and individual sgRNA-containing lentiviruses were produced in HEK293T cells seeded overnight at $4\times10^6$ cells per 10 cm dish. 1 h prior to transfection, medium was changed to fresh pre-warmed D10, followed by transfection of psPAX2, pLentiCas9-Blast or LV04, and pCMV-VSV-G at a 10:10:1 ratio. Medium was changed to fresh D10 6 hours after transfection, and supernatant virus was harvested 48 hours later, clarified by centrifugation at 2,000 RPM for 5 min in Sorvall tabletop centrifuge, and filtered through a 0.45 micron filter. Large-scale GeCKO lentivirus was produced as previously described (Joung et al., 2017, Nat. Protoc., 12:828-63).

Briefly, V2A and V2B were produced as individual lentiviral library preps using a large scale transfection of the protocol described herein, in Corning HYPERflask culture vessels. Supernatant virus was collected at Day 2 and Day 3 post transfection, filtered through a 0.45 micron filter, and concentrated by ultracentrifugation at 24,000 PRM for 2 hours at 4° C. in SW-28 rotor.

Cell lines were seeded at $1\times10^6$ cells per well of a 6 well plate the night prior to transduction. Cells were transduced by spinfection for 30 min at 25° C. and 2,500 RPM in tabletop using 1 mL per well of supernatant lentivirus in the presence of 8 µg/µL Polybrene (ThermoFisher Scientific, Cat#TR1003G). Medium was changed to fresh D10 following spinfection, and one day later, stably transduced cells were selected using 5 µg/µL puromycin (Sigma Aldrich, Cat#P9620) for 2 days.

Cas9 cells were transduced with lentivirus expressing individual targeting sgRNA (LV04 constructs) as described herein. After at least 1 week of puromycin selection, individual cell clones were plated by limiting dilution in 96-well plates in DMEM 20% FBS plus non-essential amino acids and Pen/Strep to increase cell survival. 2-3 weeks after plating single-cell clones were expanded and screened for knock-out.

Concentrated lentiCRISPR library was tittered on Huh7 AAVR KO Cas9 cells by determining % transduced cell survival after 2 days of puromycin selection, relative to untransduced control cells in the absence of puromycin.

Huh7 AAVR KO Cas9 cells were transduced with concentrated V2A or V2B lentivirus at an MOI of 0.3 in 6-well plates by spinfection as described above for 30 min at 25° C. with 8 µg/µL polybrene, followed by incubation at 25° C. and 5% $CO_2$ for 1.5, after which fresh D10 media was added. Puromycin was added at a concentration of 5 µg/µL 24 h post-transduction to select sgRNA expressing cells. Cells were cultured with puromycin for 1 week to carry out selection and allow editing to occur before selection with AAV. 30 million cells from each half of the mutagenized library (V2A and V2B cells) were transduced with 100,000 VG/cell rh32.33CMV.eGFP.WPRE. Cells were transduced in a total volume of 10 mL serum-free DMEM in each of two 15 cm plates for 1 hour followed by addition of 10 mL DMEM 20% FBS and cells were split the following day.

Cells were collected for FACS sorting by trypsinization, spun in a table-top centrifuge at 2,000 RPM for 5 min, then resuspended in PBS (without calcium and magnesium) with 5 mM EDTA. FACS sorting was done at the Massachusetts General Hospital Flow Cytometry Core (Simches Research Building) on a BD FACSAria Fusion Cell Sorter instrument. Cells were collected into DMEM supplemented with 20% FBS and Pen/Strep. Selected cells were expanded and genomic DNA was extracted from a total of $10^7$ cells per sample. GFP negative cells from each half of the library were split in half and either sequenced or subjected to a second transduction and FACS sort using the same transduction protocol.

After sequencing, raw reads were mapped to known sgRNA sequences using the MaGECK analysis pipeline. Significance values were determined for the entire library after normalization to control population within each half of the library (V2A and V2B), and data is reported as raw p-value without multiple test correction.

These genetically modified cells served as a library of cells that were next interrogated whether the genetic modification affected AAV efficiency of targeting. The sequencing of the sgRNA then permitted tracking the genetic modifications that led to an increase or decrease of AAV efficiency of targeting. This correlation was then statistically challenged for robustness. Significant hits were further validated for their role in AAV transduction. In addition, as described in Example 2, a second round of selection was performed on the library, to further increase the robustness of the findings.

Example 2

Entry Screen Identifies rh32.33 Entry Factors

Figure 2A:
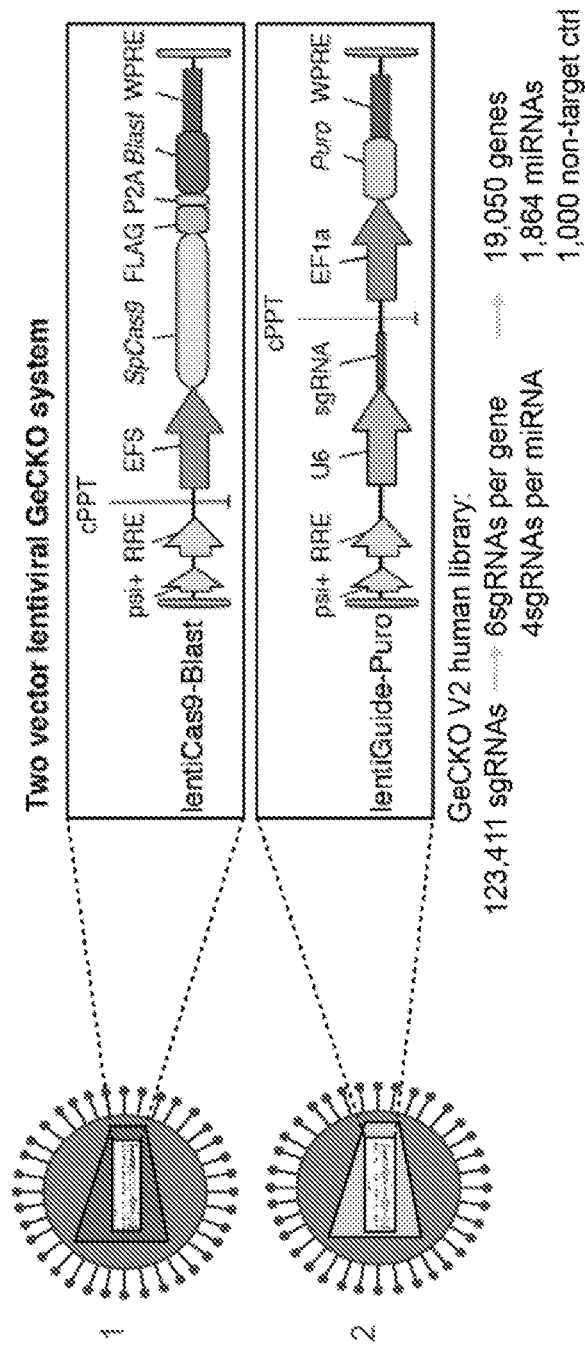
FIG. 2A is a schematic of a two-vector lentiviral GeCKO system.

A CRISPR-based entry screen was designed to identify cellular entry factors required for the alternate AAV entry pathway. A two-vector lentiviral GeCKO system introduced Cas9 in a single vector into the cell line of interest, followed by the introduction of a library of sgRNAs and miRNAs spanning the entire human genome (FIG. 2A) (Shalem et al., 2014, Science, 343:84-7). Briefly, cells were transduced with Vector 1 [lentiCas9-Blast] followed by blasticidin selection, for stable expression or Cas9. Cas9 was then transduced with Vector 2 (lentiGuide-Puro) in a library format containing sgRNAs targeting the entire human genome to generate a cell line knock-out library.

Lentiviral plasmids were purchased from Addgene or Sigma. LentiCas9-blast (52962), psPAX2 (12260), pCMV-VSV-G (8454), GeCKO V2A and GeCKO V2B (1000000048 and 1000000049) were purchased from Addgene. Individual sgRNA lentivirus constructs targeting an individual gene used for screen validation and knock-out experiments were purchased from Sigma as QuickPick glycerol stock clones in Sigma LV04 vector backbone.

Lentivirus was produced from HEK293T cells (ATCC, Manassas, VA) by transient transfection using PolyJet In Vitro DNA Transfection Reagent (SignaGen, Cat#SL100688) using manufacturer's protocol for lentiviral production. LentiCas9-blast and individual sgRNA-containing lentiviruses were produced in HEK293T cells seeded overnight at $4 \times 10^6$ cells per 10 cm dish. 1 h prior to transfection, medium was changed to fresh pre-warmed D10, followed by transfection of psPAX2, pLentiCas9-Blast or LV04, and pCMV-VSV-G at a 10:10:1 ratio. Medium was changed to flesh D10 6 hours after transfection, and supernatant virus was harvested 48 hours later, clarified by centrifugation at 2,000 RPM for 5 min in Sorvall tabletop centrifuge, and filtered through a 0.45 micron Large-scale GeC KO lentivirus was produced as previously described (Joung et al., 2017, Nat. Protoc., 12:828-63).

Briefly, V2A and V2B were produced as individual lentiviral library preps using a large scale transfection of the protocol described above, in Corning HYPERflask culture vessels. Supernatant virus was collected at Day 2 and Day 3 post transfection, filtered through a 0.45 micron filter, and concentrated by ultracentrifugation at 24,000 PRM for 2 hours at 4° C. in SW-28 rotor. Concentrated lentiCRISPR library was tittered on Huh7 AAVR KO Cas9 cells by determining transduced cell survival after 2 days of puromycin selection, relative to untransduced control cells in the absence of puromycin.

Figure 2B:
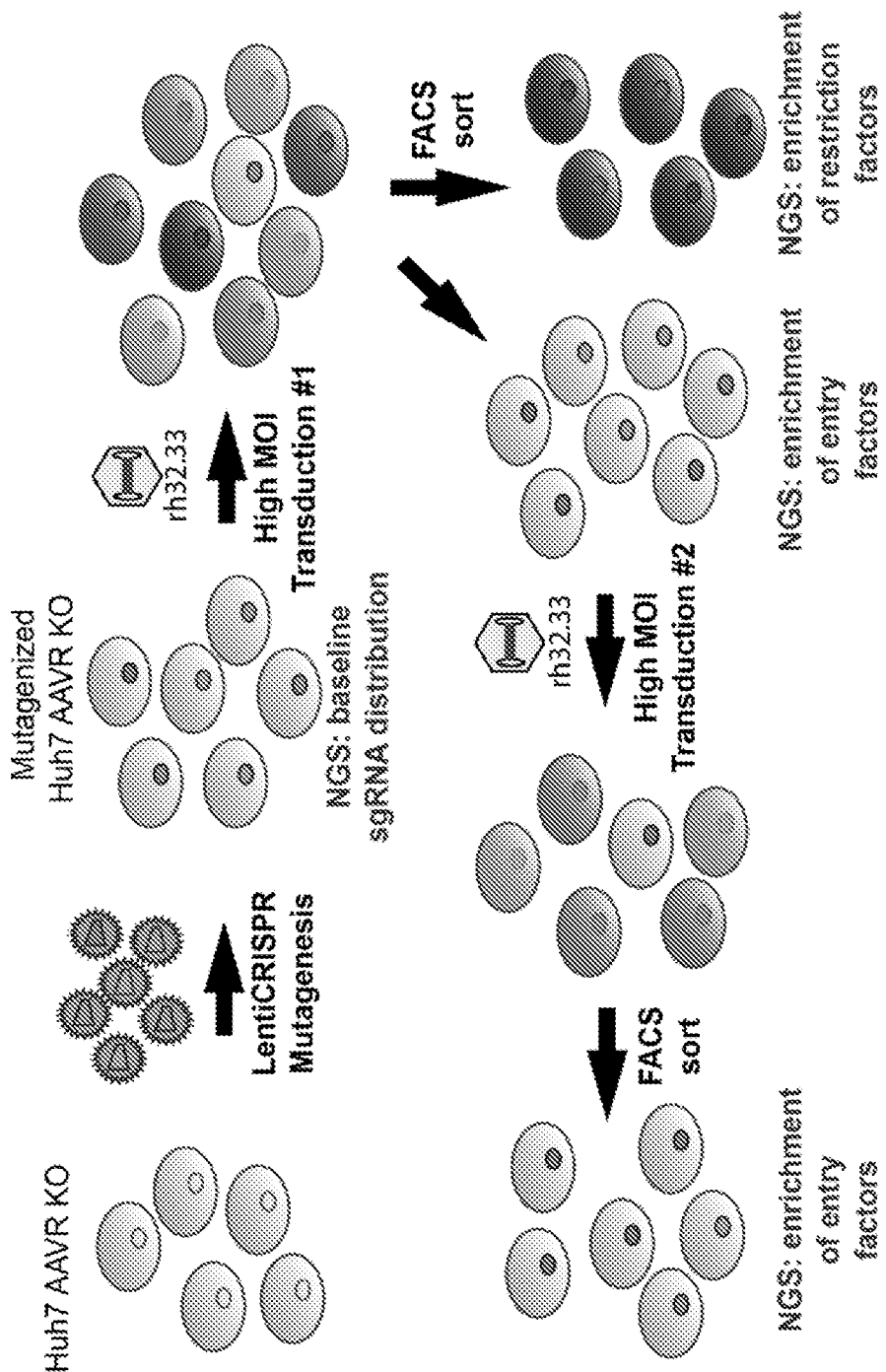
FIG. 2B is a schematic demonstrating that Huh7 AAVR KO cells undergo lentiCRISPR mutagenesis using vectors described in FIG. 2A.

Huh7 AAVR KO cells were used for this screen to assure that any possible redundancy with AAVR-dependent entry would not cause false negatives in the screen. Multiple rounds of transduction of lentiCRISPR mutagenized cells transduced with a rh32.33.CMV.eGFP.WPRE, vector and FACS sorting followed by Illumina deep sequencing of sgRNA prevalence were used to identify cellular factors involved in either AAV restriction or AAV entry (FIG. 2B).

Genomic DNA from control (unselected) or selected cells was extracted using a Qiagen Blood & Cell Culture DNA Midi Kit (Cat. No. 13343). Barcode addition and Illumina adapter addition was carried out as previously described (Joung et al., 2017, Nat. Protoc., 12:828-63). Briefly, a two-step PCR was carried out using sample-specific primers to specifically amplify sgRNA sequence and distinguish samples during multiplexed sequencing on an Illumina MiSeq machine as described (Joung et al., 2017, Nat. Protoc., 12:828-63).

Figures 3A, 3B, 3C, 3D:
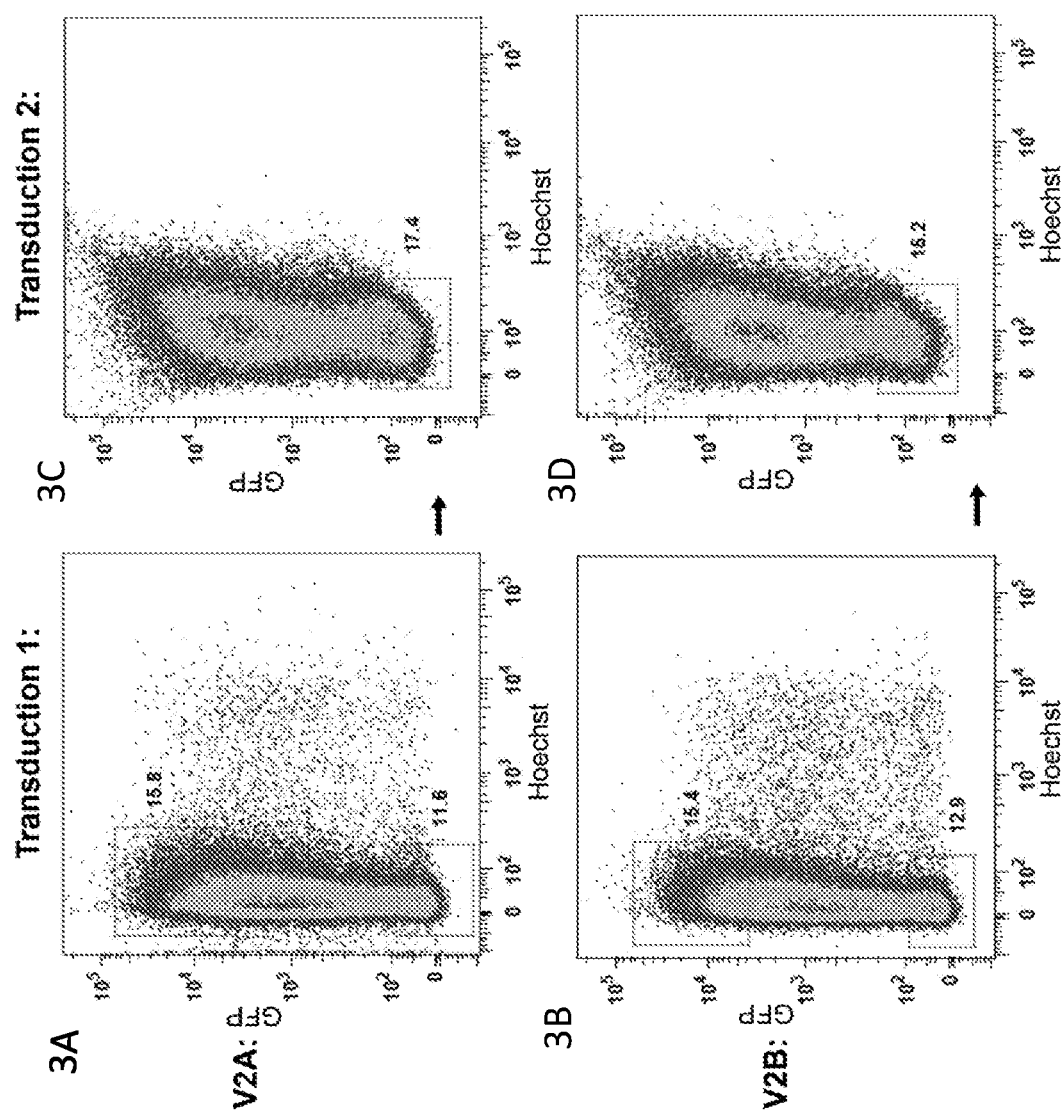
FIG. 3A is a dot plot showing FACS selection of GFP+ and GFP− cells in the V2A half of a Genome-Scale CRISPR Knock-Out (GeCKO) library.
FIG. 3B is a dot plot showing FACS selection of GFP+ and GFP− cells in the V2B half of a Genome-Scale CRISPR Knock-Out (GeCKO) library.
FIG. 3C is a dot plot showing FACS selection of GFP− cells expanded and subjected to a second round of high MOI transduction for the V2A half of the GeCKO library.
FIG. 3D is a dot plot showing FACS selection of GFP− cells expanded and subjected to a second round of high MOI transduction for the V2B half of the GeCKO library.

30 million cells mutagenized with each half of the lentiCRISPR (GeCKO) library (V2A cells and V2B cells) (Sanjana et al., 2014, Nat. Methods, 11:783-4) were transduced with a high MOI of rh32.33.CMV.eGPF.WPRE. The cells with the highest ~15% mean fluorescence intensity (MFI) were selected and sgRNA prevalence was deep sequenced to identify cellular factors that may be restricting AAV entry or gene expression (FIGS. 3A, 3B). Cells that were GFP negative (FIGS. 3A-3B) were selected, split in half and either deep sequenced or subjected to another round of transduction. These cells were transduced at the same MOI and GFP negative cells were sorted and sequenced for further enrichment of rh32.33 entry factors (FIGS. 3C, 3D). The second round of transduction, although done at the same MOI, had a higher percentage of cells that remained GFP negative (FIGS. 3C, 3D) relative to the first found of transduction (FIGS. 3A, 3B), suggesting that selection enriched for deleted genes required for rh32.33 entry. The genomic DNA was extracted from the different selected cell populations, and the sgRNAs were amplified by a two-step nested-PCR strategy that added sample-specific barcodes and Illumina adaptors (Joung et al., 2017, Nat. Protoc., 12:828-63) for deep sequencing The samples were multiplexed and sequenced, followed by combining the V2A and V2B samples to analyze the sgRNA prevalence in the full library, and reads were mapped back to known sequences within the lentiCRISPR V2 library. A two-step nested PCR strategy was used to amplify sgRNA's for sequencing from unselected (ctrl) or first round GFP+ or GFP– cell populations, adding a unique sample barcode and Illumina adaptors in the NGS amplicon. Each selection condition produced more than 7 million total raw reads and more than 3.7 million reads mapped perfectly to the known input sgRNA sequence, enough to maintain greater than 300-fold coverage of the sgRNA library.

In this second round of selection for cells that were made refractory to AAV infection by genetic perturbation, a more rigorous selection was performed to identify, through this multiplex library approach, which cellular factors are associated with reduced AAV infection. These co-factors, identified by the sequencing of sgRNA markers in the host genome, are then considered potential required genes and proteins involved in AAV transduction.

Example 3

Identification of Potential AAV Restriction Factors

Robust Rank Aggregation (RRA) analysis and MAGeCK analysis (Li et al., 2014, Genome Biol., 15:554; and Li et al., 2015, Genome Biol., 16:281) of the GFP positive cells identified several factors enriched in the cells with high mean fluorescence intensity (FIG. 4A):

ACSL6: Acyl-CoA Synthetase Long Chain Family Member 6, catalyzes the formation of Acyl-CoA from fatty acids and may playing a major role in lipid metabolism.

LETMD1: LETM1 Domain Containing 1, has been suggested to have a role in p53 regulation and tumorigenesis.

CALN1 Calneuron 1, negatively regulates golgi-to plasma membrane transport, deletion of which could potentially alter the trafficking pathways upon AAV transport to the nucleus.

SSH3: Slingshot Protein Phosphatase 3, plays a role in actin dynamics by activating ADF/cofilin proteins, which may also influence and alter the AAV entry trafficking pathways.

The most significant hit in the GFP positive subset was TMEM125, an uncharacterized transmembrane protein. Individual sgRNA(s) targeting several of the top hits from the GFP positive selection were introduced to Huh7 AAVR KO Cas9 cells using a lentiviral vector, then puromycin-selected cells were assessed for rh32.33 transduction level using a luciferase assay.

Data presented are fold increase in RLU from transduction of 10,000 VG/cell with rh32.33.CMV.Luciferase.SVPA in CRISPR edited polyclonal cell population relative to parental cell line (Huh7 AAVR KO Cas9). Polyclonal cell lines were generated by transduction of Huh7 AAVR KO Cas9 cells with lentivirus encoding sgRNAs targeting individual genes identified in rh32.33 GFP+ cell population. Several sgRNA transduced cell lines demonstrated increased transduction relative to the parental cell line, most notably TMEM125 and GMEB2 (glucocorticoid modulatory element binding protein 2), which each showed roughly a 100-fold increase in transduction (FIG. 4B).

This results demonstrate that GeCKO-based entry screen is able to identify potential cellular restriction factors for AAVrh32.33.

Example 4

Identification of Potential AAV Entry Factors

Figures 5A, 5B:
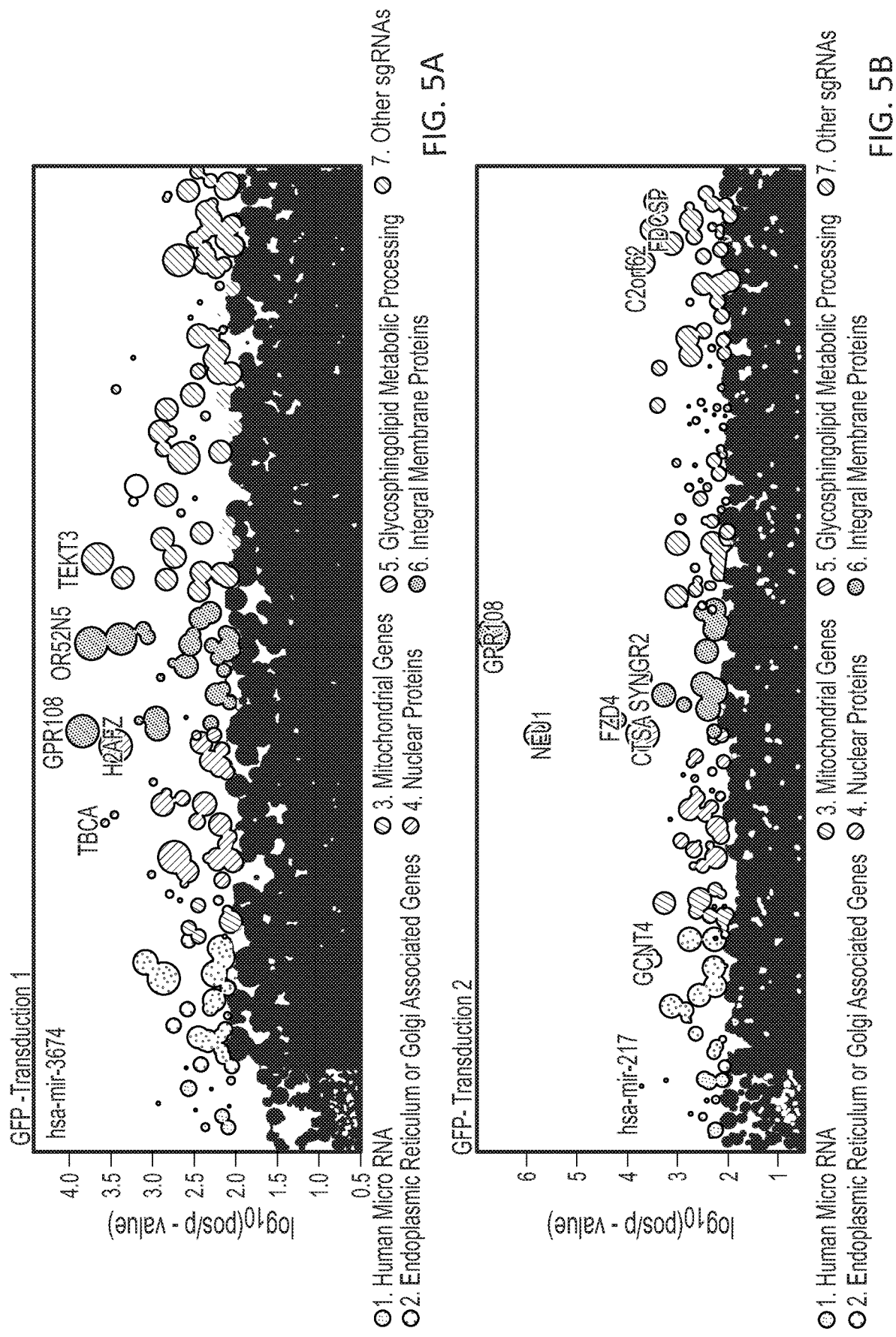
FIG. 5A is the RRA of the first round of GFP− transduction, grouped by functionality.
FIG. 5B is the RRA of the second round of GFP− transduction, grouped by functionality.

Analysis of the GFP− cell population produced as described herein identified several genes that were enriched in the GFP− population, one of the most significant of which was GPR108 (FIG. 5A). This gene was even further enriched in the analysis of the second round of transduction (FIG. 5B), as well as other genes that were highly enriched such as neuraminidase 1 (NEU1) and cathepsin A (CTSA). The X-axis indicates the individual genes within the GeCKO library grouped by functionality, and the Y-axis indicates the significance of each hit based on RRA analysis. The bubble diameter corresponds to the number of individual sgRNAs per gene enriched in the selected population, relative to the unselected control. Importantly, the significance of the top hits increased to a p-value of near $10^6$, while other genes stayed the same, around a significance value of $10^3$. This suggests that the second round of transduction was extremely important for the enrichment of rh32.33 entry factors. The identification of GPR108 as an entry factor led to the investigation and mapping of the VP1 region involved in GPR108 dependence.

Example 5

NEU1 and CTSA Are Required for Entry of Alternate Entry Pathway Serotypes rh32.33 and AAV4

Figures 6A, 6B, 6C, 6D, 6E, 6F, 6G:
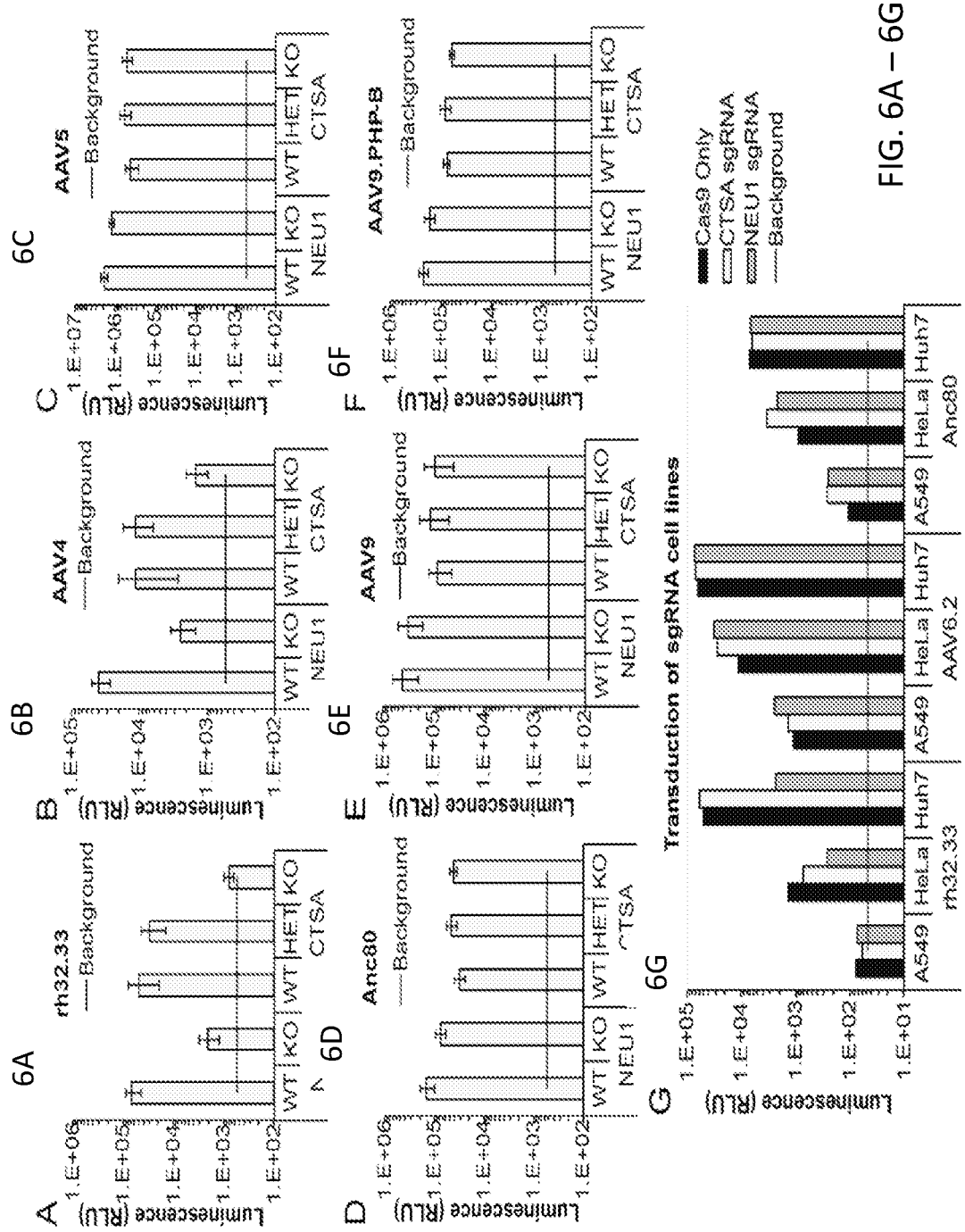
FIGS. 6A-6F are graphs of the luminescence observed in WT (wild type), Neuraminidase 1 (NEU1) knock-out [KO], cathepsin A (CTSA) heterozygous (HET) of CTSA knock-out [KO] cells transduced with AAVR independent serotypes rh32.33 or AAV4 (6A, 6B) or AAVR independent serotypes AAV5, Anc80, AAV9, or AAV9.PHP-B (6C-6F) in the presence of hAd5 helper virus.
FIG. 6G is a graph of the luminescence observed in various human cell lines expressing Cas9 transduced with as lentivirus containing CTSA- or NEU1-specific sgRNA followed by transduction of different AAV capsids expressing the CMV.Luciferase.SVPA transgene.

Since NEU1 and CTSA exist in a complex together, and NEU1 stability and conformation is dependent on CTSA (Galijart et al., 1988, Cell, 54:755-64; and Bonten et at, 1995, J. Biol. Chem., 270:26441-5), these proteins were tested to determine whether both are important for the alternate AAV entry route. Two AAVR independent serotypes were tested, rh32.33 and AAV4, in previously published Mouse Embryonic Fibroblast (MEF) cell lines derived from either NEU1 WT or KO mice, or CTSA WT, Heterozygous (HET), or KO mice. Both rh32.33 and AAV4 showed a loss of transduction in the NEU1 and CTSA KO cells, with little or no effect being observed in the CTSA heterozygous cells (FIGS. 6A, 6B).

Several other AAV serotypes were tested, including AAV5, which uses sialic acid as an attachment factor. Although NEU1 is involved in sialic acid glycan biology, no difference in transduction of any AAVR dependent serotypes was observed (FIGS. 6C-6F). This demonstrates that NEU1 and CTSA are specifically required for AAVR independent entry, and that rh32.33 and AAV4 appear to use the same alternate entry pathway. The effect of NEU1 loss in human cells was further evaluated by introducing either an NEU1- or CTSA-specific sgRNA into a variety of Cas9 cell lines. Although a monoclonal cell line with complete NEU1 knock-out functionality was not identified, when cells were tested after puromycin selection in a polyclonal context, a large decrease in rh32.33 transduction was observed in multiple NEU1 sgRNA transduced cell lines but no decrease was observed for any other serotypes tested (FIG. 6G). This suggests that NEU1 is required for AAVR independent entry in both human and mouse cells.

Example 6

Enzymatic Activity of NEU1 is Required for Alternate Pathway Entry

Because NEU1 is an enzyme and CTSA, also identified in the entry screen (FIG. 5C), is required for maintaining the catalytically active conformation of NEU1 (D'Azzo et al., 1982, PNAS USA, 79:4535-9; and Vinogradova et al., 1998, Biochem. J. 330(Pt 2):641-50), whether enzymatic activity of NEU1 is required for its function was tested in rh32.33 and AAV4 entry. Two different sialic acid analog neuraminidase inhibitor compounds were used, Zanamivir (von Itzstein et al., 1993, Nature, 363:418-23) and DANA (Meindl et al., 1974, Virology, 58:457-63), to do a dose response on Huh7 cells and assess the effect on entry of different AAVR dependent and AAVR independent serotypes. Two different AAVR-dependent serotypes, AAV5 and Anc80, and two AAVR-independent serotypes, rh32.33 and AAV4, were tested. Importantly, AAV4 and AAV5 were examined because both AAVs use sialic acid as an attachment factor (Kaludov et al., 2001, J. Virol., 75:6884-93; and Walters et at, 2001, J. Biol. Chem., 276:20610-6) yet differ in their AAVR dependence.

Briefly, 10,000 cells per well were plated in 96-well plates 1 day prior to inhibitor treatment. Cells were incubated with the indicated concentration of Zanamivir (Sigma SML0492) or DANA (EMD Millipore 252926) for 24 hours prior to transduction in a total volume of 100 µL D10. When indicated, control or inhibitor treated cells were treated with 50 mU/mL Neuraminidase from *Vibrio cholera* Type III (Sigma Aldrich, Cat#N7885) in serum-free DMEM, followed by AAV transduction as described.

Figures 7A, 7B:
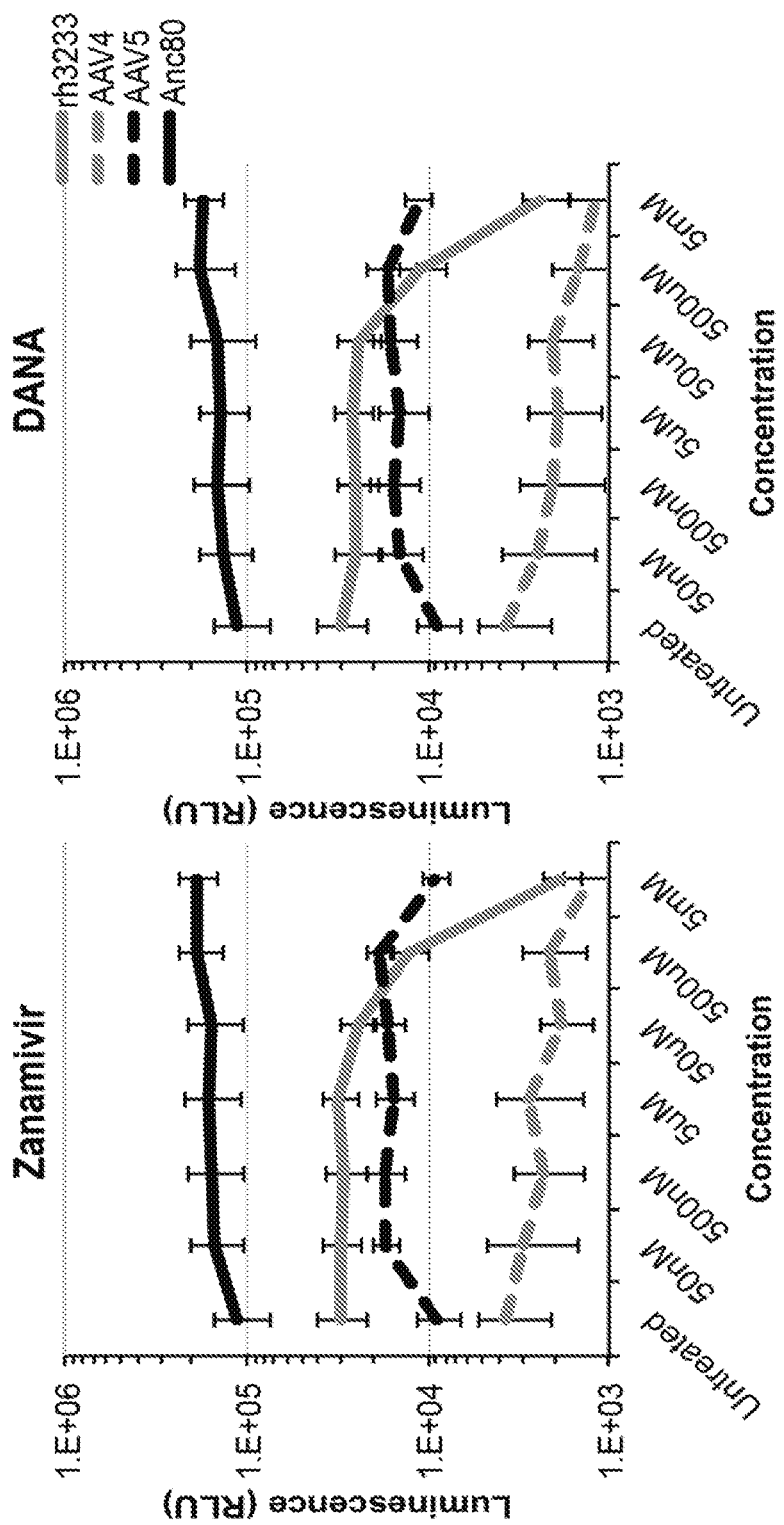
FIGS. 7A and 7B are graphs of the luminescence observed in Huh7 cells pre-treated with the indicated concentrations of neuraminidase inhibitors, Zanamivir (7A) or DANA (7B), followed by transduction of the indicated capsid serotype encapsidating a luciferase-encoding transgene (dark: AAVR-dependent serotypes; light: AAVR-independent serotypes; solid line: unknown glycan attachment factor; dotted line: sialic acid used for attachment).

A short, 1 hour pre-treatment of cells did not show any decrease in transduction. However, pie-treatment of Huh7 cells for 24 hours with the indicated concentrations of the neuraminidase inhibitors, Zanamivir (FIG. 7A) or DANA (FIG. 7B) followed by transduction of 10,000 VG/cell of the indicated capsid serotype encapsidating a CMV.Luciferase.SVPA transgene drastically decreased rh32.33 transduction by roughly ten-fold, as well as slightly decreased AAV4 entry (black: AAVR-dependent serotypes; green: AAVR-independent serotypes; solid line: unknown glycan attachment factor; dotted line: sialic acid used for attachment). The requirement for long pre-incubation with neuraminidase inhibitors to show a decrease in AAVR-independent entry suggests that the entry defect may be secondary to NEU1 and CTSA function, in the sense that NEU1 activity may be regulating activity of another protein or cellular process required for entry. Neither of the AAVR-dependent serotypes, AAV5 or Anc80, showed a decrease in transduction, demonstrating that the activity of NEU1 is specifically required for entry of AAVR-independent serotypes.

Because NEU1 and CTSA play a role in cellular glycosylation states, confirmation was desired that the entry defect was not due to an overall alteration in glycosylation at the cell surface, leading to an attachment, defect. To do this, cells were first pre-treated for 24 h with Zanamivir or DANA, followed by treatment with a neuraminidase from *Vibrio cholera* to remove any sialic acid that may have accumulated at the cell surface due to NEU1 inhibition.

The indicated pre-chilled vector was then added to cells on ice, incubated for 1 hour for the vectors to undergo attachment, unbound vector was washed away using ice-cold PBS, then transduction was allowed to proceed and vector transduction assessed in the different treatment conditions by fold-change relative to untreated control cells via luciferase assay.

The same four vectors used in FIG. 7 were examined, to tease apart the function of NEU1 on attachment verses entry of these different serotypes. The indicated cell lines were plated on 24-well plates at $5 \times 10^4$ cells per well overnight. Cells were placed on ice for 10 minutes, then $10^9$ VG per well pre-chilled vector was added in a total volume of 200 µL per well. Vectors were allowed to bind cells on ice on an orbital shaker platform for 1 h. Following binding, cells were washed 3× with ice-cold PBS with $Mg^{2+}$ and $Ca^{2+}$ then either 100 µL PBS per well was added and plates were frozen at ~80° C. Binding assay plates underwent 3 freeze-thaw cycles, prior to resuspension and viral genome quantification by qPCR as described herein using CMV primer/probe.

DNase1-resistant viral genomes of iodixanol purified vector preps were quantified by TaqMan qPCR (ThermoFisher, Cat#4304449) using a primer and probe set detecting CMV promoter. Vector purity was assessed by SDS-PAGE electrophoresis.

Figures 8A, 8B, 8C, 8D, 8E:
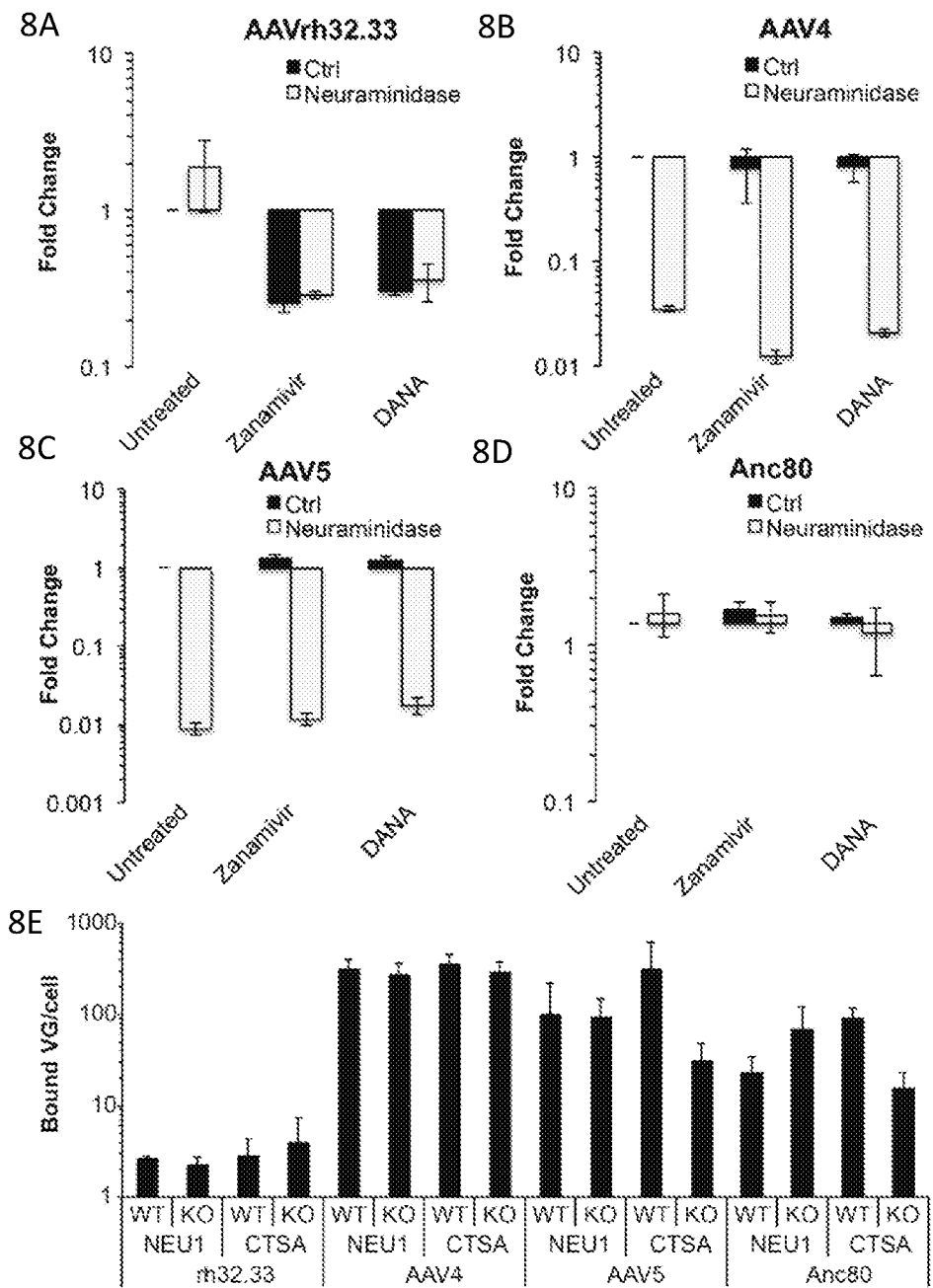
FIGS. 8A-8D are graphs of the luminescence observed in Huh7 cells pre-treated with 2 mM of the indicated compound, followed by a 2 h treatment with Neuraminidase from *Vibrio cholera* before transduction with rh32.33 (8A), AAV4 (8B), AAV5 (8C), or Anc80 (8D) encapsidating a luciferase-encoring transgene.
FIG. 8E is a bar graph of cell-bound viral genomes in WT and mutant MEF cell lines for the indicated serotypes.

Huh7 cells were pre-treated for 24 h with 2 mM of Zanamivir or DANA, followed by a 2 h treatment with Neuraminidase from *Vibrio cholera* before transduction with rh32.33 (FIG. 8A), AAV4 (FIG. 8B), AAV5 (FIG. 8C), or Anc80 (FIG. 8D) encapsulating a CMV.Luciferase.SVPA transgene. FIG. 8E are the results of qPCR cell-bound viral genomes on WT and mutant MEF cell lines for the indicated serotypes.

After neuraminidase treatment of Zanamivir- or DANA-treated cells, a reversal of entry inhibition was not observed (FIG. 8A), suggesting that the rh32.33 entry defect is not due to altered glycan structure at the cell surface. In contrast, AAV 4 and AAV5 both showed a drastic drop in transduction after treatment with exogenous neuraminidase, as expected due to a loss of their preferred glycan attachment factor, a terminal sialic acid moiety (FIGS. 8B, 8C). Because Anc80 has no known attachment factor and uses AAVR, no effect of NEU1 inhibition or neuraminidase treatment was observed on overall transduction of Anc80, as expected (FIG. 8D). These data suggest that the NEU1 and CTSA entry defect is likely not due to global perturbation of glycan structure on the cell surface. To assay vector attachment directly, a qPCR based cellular binding assay was used to measure vector attachment to NEU1 and CTSA WT or KO MEF cells.

While differences in attachment of the different vectors was demonstrated (e.g., roughly 100-fold increase in attachment of AAV4 compared to rh32.33 (FIG. 8E)), a major difference in WT vs. NEU1 or CTSA KO cells was not observed for any of the vectors tested. This binding assay demonstrates that a loss of transduction in NEU1 and CTSA KO cells is not due to a defect in attachment of the vector at the cell surface and that these proteins likely play a post-attachment role as an entry receptor or part of a multi-protein entry-receptor complex.

Example 7

GPR108 is Required for Entry of AAVR Dependent and AAVR Independent Serotypes in Multiple Cell Types The most significantly enriched gene identified in this screen was an uncharacterized 7 transmembrane G-protein coupled receptor-like protein, GPR108 (FIGS. 5A, 5B). GPR108 is required for entry of all serotypes but AAV5, and is independent of helper virus.

Interestingly, this protein was also identified as a potential entry factor in the initial haploid screen that identified AAVR (Pillay et al., 2016, Nature, 530:198-12). This suggested to us that GPR108 may be important not only for rh32.33 entry, but for entry of other AAV serotypes as well. A GPR108 KO Huh7 cell line was generated and a panel of extant serotypes as well as putative ancestral intermediate capsids were tested (FIG. 9A) for GPR108 usage via luciferase assay.

Figures 9A, 9B, 9C:
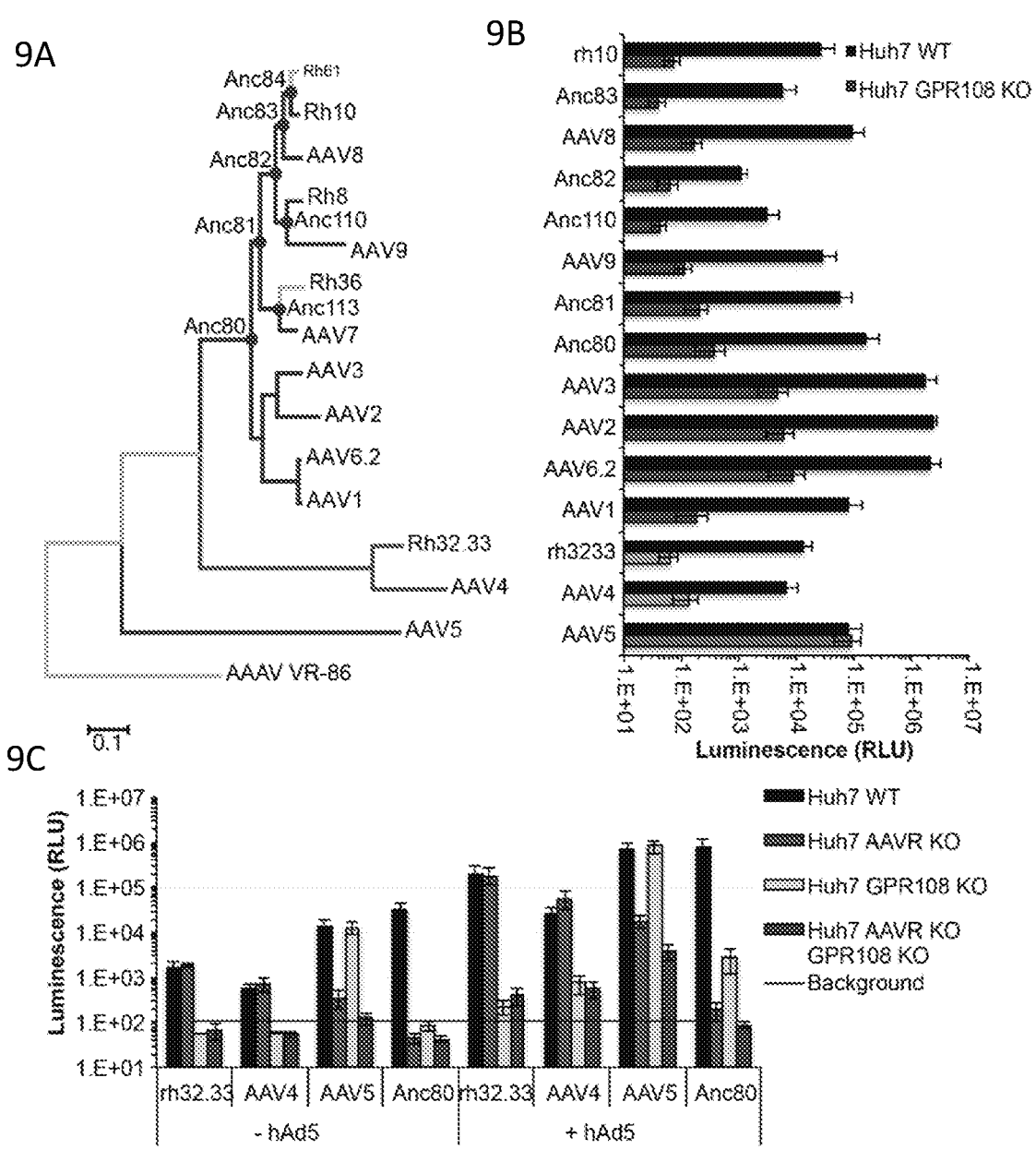
FIG. 9A is a phylogenetic tree of extant and putative evolutionary intermediate AAV serotypes.
FIG. 9B is a graph of the luminescence observed in WT or GPR108 KO Huh7 cells transduced with a CMV.Luciferase.SVPA (AAVrh10, AAV8, AAVAnc82, AAV9, AAVAnc81, AAVAnc80, AAV3, AAV6.2, AAV1, AAVrh32.33, AAV4, AAV5) or a CMV.eGFP.T2A.Luciferase.SVPA (AAVAnc83, AAVAnc110, AAV2) transgene.
FIG. 9C is a graph of the transduction level of indicated serotypes in AAVR KO, GPR108 KO, or double KO cells relative to WT Huh7 cells.

Transduction of all tested serotypes (CMV.Luciferase.SVPA (AAVrh10, AAV8, AAVAnc82, AAV9, AAVAnc81, AAVAnc80, AAV3, AAV6.2, AAV1, AAVrh32.33, AAV4, AAV5) or CMV.eGFP.T2A.Luciferase.SVPA (AAVAnc83, AAVAnc110, AAV2)) WT or GPR108 KO Huh7 cells at 10,000 VG/cell with hAd5 helper virus except AAV5 was greater than 10 to 100-fold decreased in the GRP108 KO cells compared to WT Huh7 cells (FIG. 9B).

In cells deleted for both AAVR and GPR108 (i.e., AAVR KO, GPR108 KO, or double KO cells relative to WT Huh7 cells in the presence or absence of helper virus), there was a complete loss of transduction of all serotypes, whether cells were pre-infected with a helper virus or not (FIG. 9C).

Loss of transduction upon GPR108 KO also was observed in H1 HeLa cells (FIG. 10A), suggesting that requirement of this cellular entry factor is conserved in all AAV transducible cell lines.

Example 8

AAV Entry Can Be Rescued by Stable or Transient Transfection of GPR108

To confirm the GPR108 KO defect is due to a loss of GPR108 protein expression, the GRP108 cDNA was stably re-introduced into H1 HeLa GPR108 KO cells using a lentiviral vector.

Figure 10A:
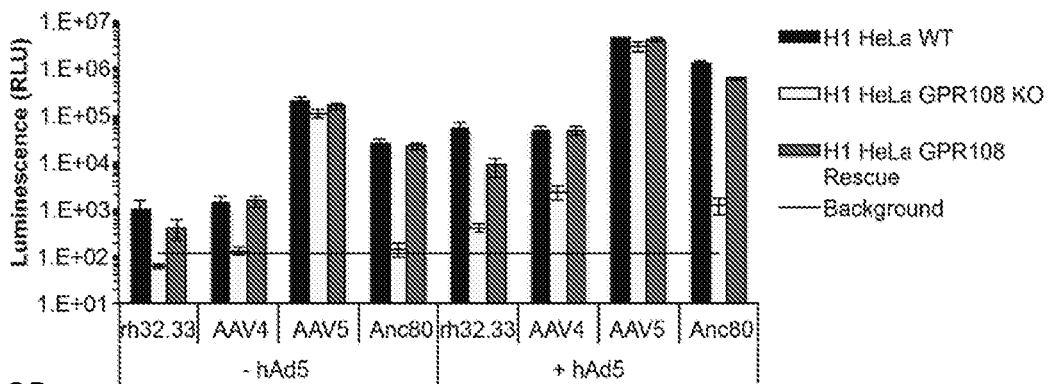
FIG. 10A is a graph of the luminescence observed in H1 HeLa cells deleted for GPR108, then stably transduced with GPR108 lentivirus, followed by transduction of the indicated serotypes expressing a luciferase-encoding transgene with and without helper virus.

H1 HeLa cells were generated in which GPR108 was deleted, then the KO cells were stably transduced with GPR108 lentivirus, followed by transduction of the indicated serotypes at 10,000 VG/cell with and without helper virus. Stable re-introduction was able to rescue transduction of all tested GPR108-dependent vectors, but KO and rescue had no effect on the overall transduction level of the GPR108-independent AAV5 (FIG. 10A). There are no functional antibodies available for detection of GPR108, so a construct containing a 3× alanine-glycine linker at the c-terminus, followed by a flag-tag for detection of GPR108 protein expression, was designed. This construct as well as a flag tagged homolog, GPR107, were sub-cloned into pcDNA3.1(−) and transiently transfected into WT or GPR108 KO Huh7 cells, followed by transduction with a variety of GPR108-dependent and independent serotypes. Expression of flag-tagged constructs was determined by Western blotting of whole-cell lysates using mouse anti-flag clone M2 antibody (Sigma F1804) and rabbit anti-beta-actin loading control (Abcam ab8227). Flag-tagged GPR107 and GPR108 constructs containing flanking NotI and BamHI restriction sites were synthesized by Genewiz, followed by restriction enzyme subcloning into pcDNA3.1(−) plasmid using NotI and BamHI (NEB) restriction sites.

Huh7 WT or GPR108 KO cells were transfected with flag-tagged human or mouse GPR107 or GPR108 followed by transduction of the indicated serotype in the presence of hAd5 helper virus (10,000 VG/cell CMV.Luciferase.SVPA transgene). Although there was not a full rescue of transduction to wild type levels, there was a clear rescue phenotype observed from transfection of GPR108, but not GPR107 (FIGS. 10B, 10C) for all GPR108-dependent serotypes. These data demonstrate that GPR108 protein expression is required for the entry pathway of most AAVs, aside from the most evolutionarily divergent serotype, AAV5.

Example 9

GPR108 Usage is Conserved in Mouse

As human and mouse GPR107 and GPR108 are highly similar sequences, we wanted to determine whether GPR108 was similarly used for AAV entry in mouse cells. Hepa cells, a mouse hepatoma cell line, were used as an analogous mouse in vitro system to the human Huh7 cells. Transduction of rh32.33, AAV4, AAV5, [FIG. 4.11.A] and Anc80, AAV9, and AAV9, PHP-B [FIG. 4.11.B] in Hepa WT or GPR108 KO cells transfected with flag-tagged human or mouse GPR107 or GPR108 (10,000 VG/cell CMV.Luciferase.SVPA transgene). Interestingly, AAV5 is able to transduce Hepa cells to a high level, while other serotypes such as rh32.33 and AAV4 are not (FIG. 11A). This suggests that the alternate factor AAV5 uses in place of GPR108 is likely conserved in mouse, yet mouse GPR108 may not be as highly functional as human GPR108 for some serotypes. An sgRNA against mouse GPR108 was additionally used to generate a Hepa GPR108 KO cell line. Of the GPR108-dependent serotypes tested that transduced Hepa cells, all demonstrated a 10- to 100-fold decrease in transduction in the hepa GPR108 KO cells compared to wild type (FIG. 11B). Flag-tagged human or mouse cDNAs of GPR108 or a homologous protein GPR107 (Edgar, 2007, DNA Seq., 18:235-41) were re-introduced into hepa GPR108 KO cells, and a slight increase in AAV transduction was observed (FIG. 11B).

Figure 10B:
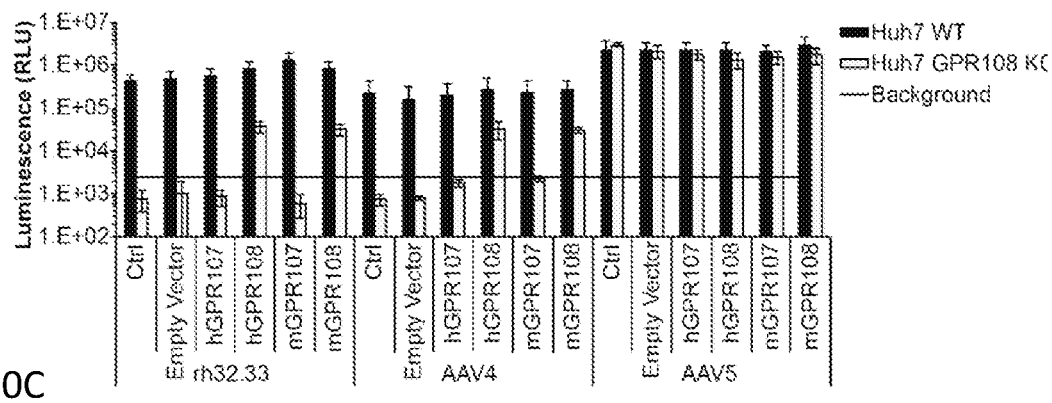
FIG. 10B is a graph of the luminescence observed in Huh7 WT or GPR108 KO cells transfected with flag-tagged human GPR107 or GPR108 followed by transduction of the indicated serotype expressing a luciferase-encoding transgene.
Figure 10C:
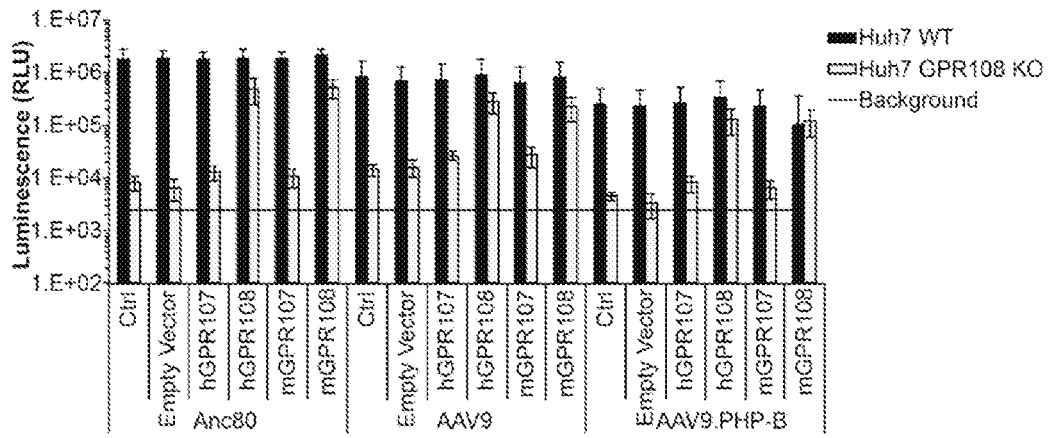
FIG. 10C is a graph of the luminescence observed in Huh7 WT or GPR108 KO cells transfected with flag-tagged mouse GPR107 or GPR108 followed by transduction of the indicated serotype expressing a luciferase-encoding transgene.

Interestingly, in human cells, mouse GPR108 is able to rescue transduction to similar levels as the human GPR108 construct (FIGS. 10B, 10C). It is possible that these constructs were not successful to rescue transduction due to low protein expression levels. Therefore, expression of each of these constructs was assessed using an anti-flag Western blot from transfected cell lysates in human and mouse cells.

Figures 12A, 12B, 12C, 12D:
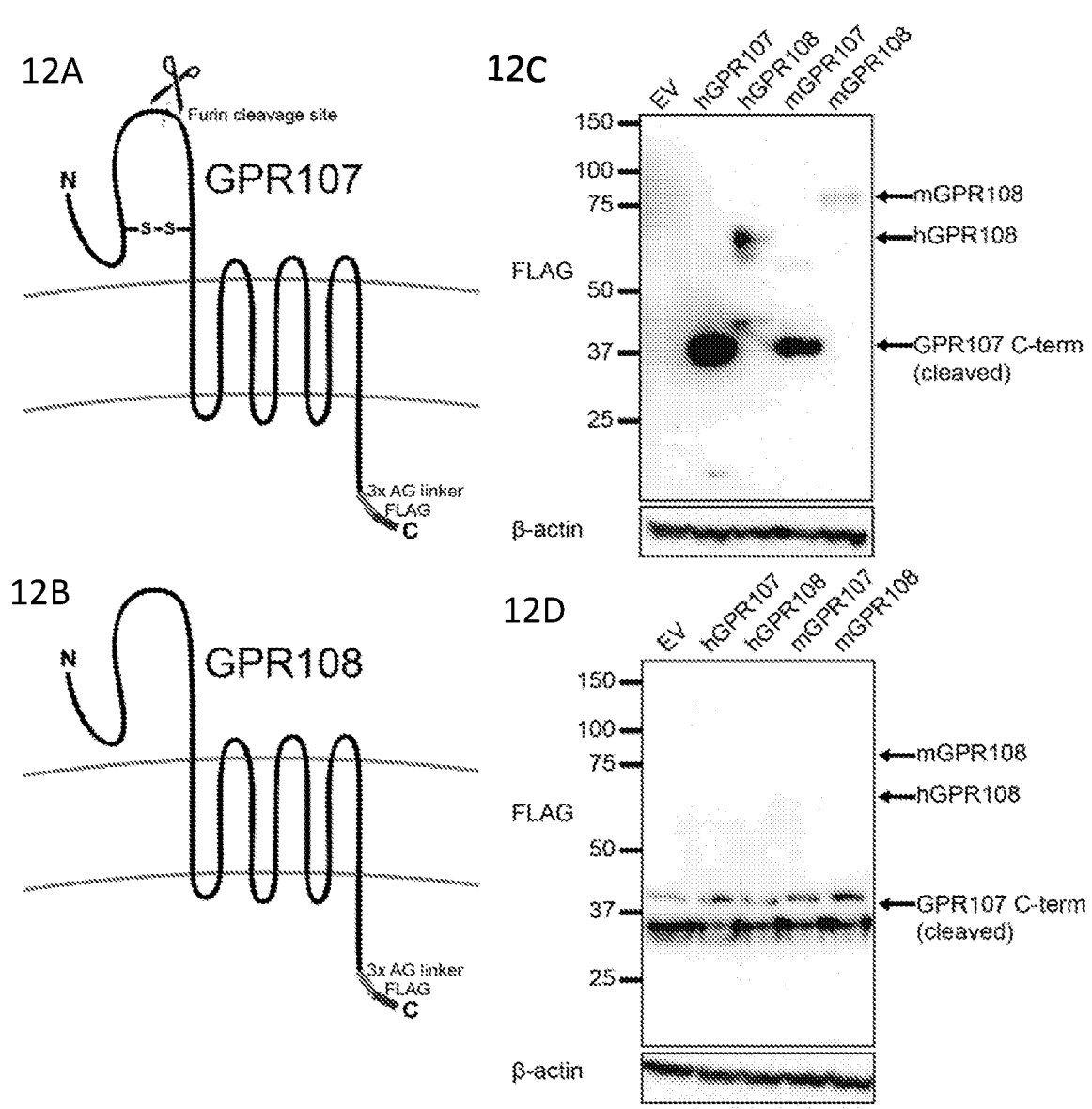
FIG. 12A is a schematic of the membrane orientation of non-functional GPR107.
FIG. 12B is a schematic of the predicted membrane orientation of GPR108.
FIG. 12C is an image of a Western blot that demonstrates the expression of human and mouse GPR107 and GPR108 constructs in Huh7 cells, visualized by a flag-tag at the C-terminus.
FIG. 12D is an image of a Western blot (probed with an anti-flag antibody) to demonstrate expression of human and mouse GPR107 and GPR108 in Hepa cells.

GPR107 and GPR108 are both relatively uncharacterized proteins predicted to have 7 transmembrane domains, with a large luminal N terminus and short cytoplasmic C terminus (FIGS. 12A, 12B). GPR107 has been shown to have both a disulfide bond and a furin cleavage site in the luminal N-terminal domain required for its function (Tafesse et al., 2014, J. Biol. Chem., 289:24005-18), and the alanine-glycine linker and flag tag also are shown (FIG. 12A). Furin cleavage of GPR108 produces two peptide fragments of roughly 28 and 34 kDa, the larger of which is visualized by anti-flag Western blot after transient transfection is Huh7 cells (FIG. 12C). The beta-actin loading control is shown in (FIG. 12D). These data demonstrate that GPR108 and GPR107 were expressed and post-translationally modified as expected.

Example 10

GPR108 Does Not Facilitate AAV Attachment

The current understanding of factors involved in AAV transduction primarily exists surrounding factors involved in AAV attachment, and there is little known about the presence and mechanism of intracellular AAV entry receptors. Therefore, we wanted to test whether GPR108 is playing a role in AAV attachment or further downstream in the entry pathway. Two different capsid surface mutants that have altered tropism or binding properties were tested, alongside their parental AAV capsid, in Huh7 and H1 HeLa GPR108 KO cells.

Figures 13A, 13B, 13C:
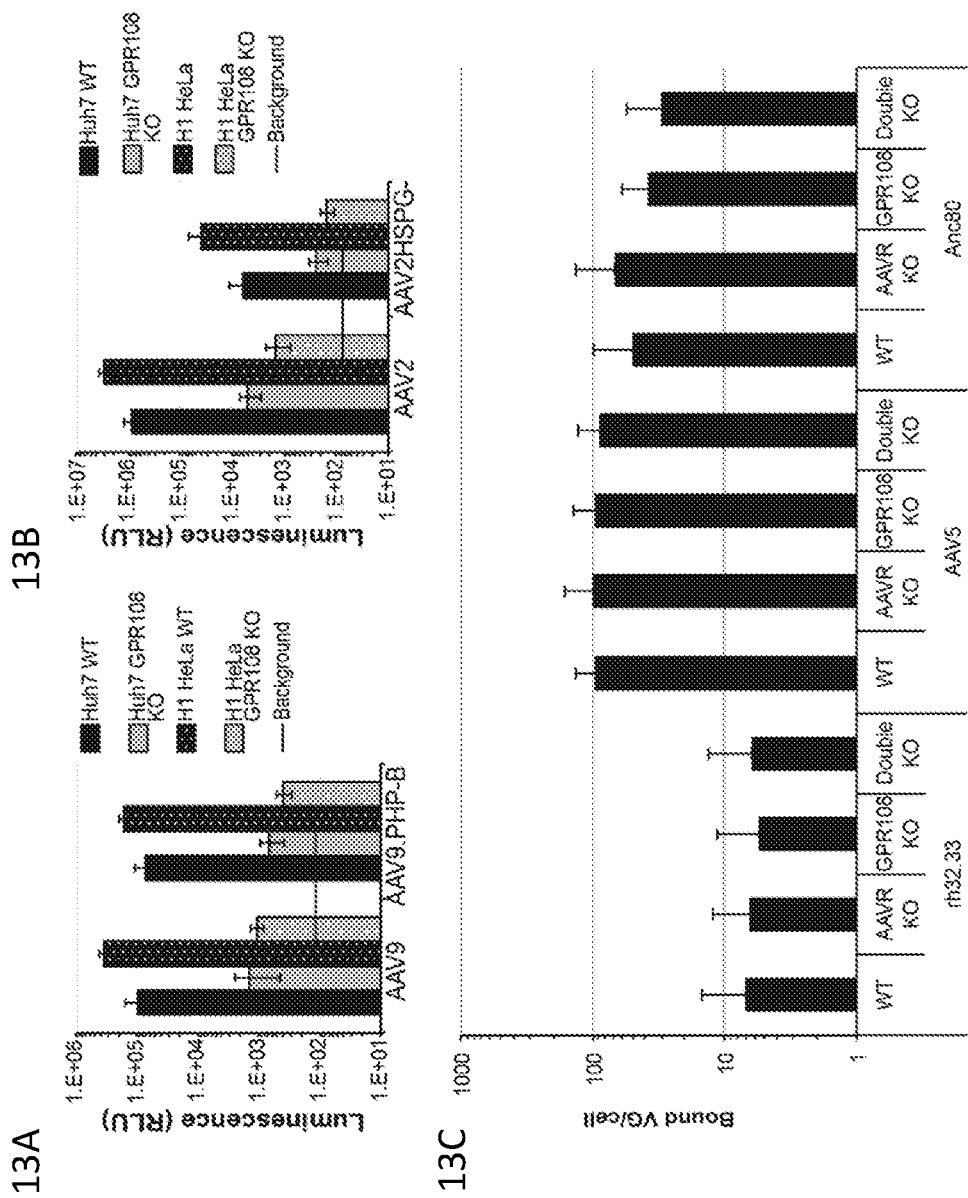
FIG. 13A is a graph of the luminescence observed in WT or GPR108 KO Huh7 or H1 HeLa cells transduced with parental capsid AAV9 or surface exposed peptide-insertion capsid AAV9.PHP-B.
FIG. 13B is a graph of the luminescence observed in WT or GPR108 KO Huh7 or H1 HeLa cells transduced with a glycan-binding defective AAV2HSPG− or parental AAV2 capsid.
FIG. 13C is a graph of a binding assay for cell-bound viral genomes in Huh7WT, AAVR KO, GPR108 KO, or double KO cells, assessed for the indicated capsid serotype.

First, a luciferase assay demonstrated that a peptide insertion variant of AAV9, AAV9.PHP-B (Deverman et al., 2016, Nat. Biotechnol., 34:204-9), transduced into WT or GPR108 KO Huh7 or H1 HeLa cells, was dependent on GPR108, similar to the parental capsid, AAV9 (FIG. 13A). Additionally, an AAV2 variant containing point mutations that ablate binding to the primary AAV2 attachment factor, heparin sulfate (Vandenberghe et al., 2006, Nat. Med., 12:967-71), was tested. While the HSPG− variant (glycan-hiding defective AAV2HSPG− or parental capsid AAV2) had overall decreased transduction in all cell lines tested (WT or GPR108 KO Huh7 or H1 HeLa cells) (FIG. 13B), transduction of the GPR108 KO cells were 10- to 100-fold decreased compared to their wild-type counterpart, suggesting that GPR108 usage is independent of AAV attachment. While these data suggest that GPR108 does not facilitate attachment, it was desired to test this directly.

Therefore, a binding assay was employed as described to assess attachment of GPR108-dependent and -independent serotypes. Huh7 WT and GPR108 KO cells were tested, as well as AAVR KO cells and the double KO cells, since AAVR was previously suggested to play a role at the plasma membrane (Pillay et al., 2016, Nature, 530:108-12) (FIG. 13C). No difference was observed in the number of bound viral genomes per cell in any of the knock-out cell lines for any vector tested, yet differences in the number of bound viral genomes for different serotypes were detected, demonstrating that GPR108 is not facilitating attachment.

Example 11

Figure 14A:
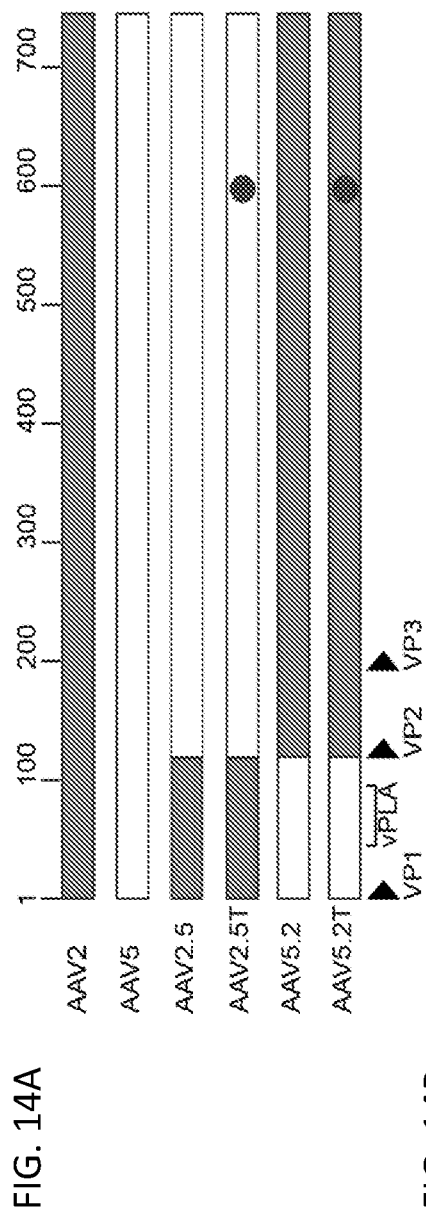
FIG. 14A is a schematic showing the chimeric capsids used to determine the GPR108 usage domain.
Figure 14B:
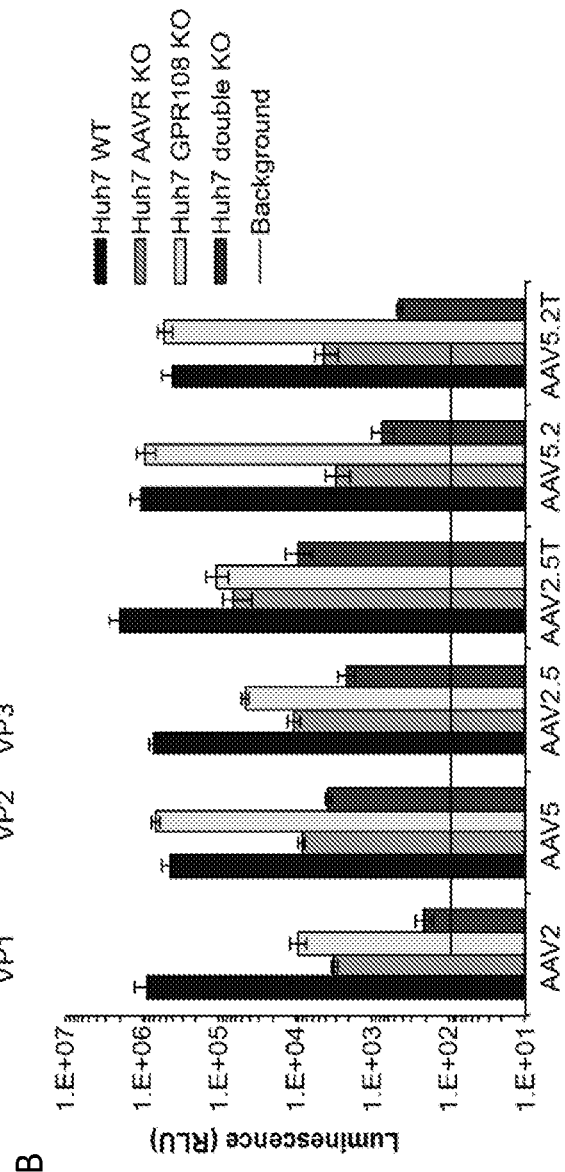
FIG. 14B is a graph of the luminescence observed in Huh7 WT, AAVR KO, GPR108 KO, or double KO cells transduced with the indicated WT or chimeric capsids expressing a luciferase-encoding transgene.

GPR108 Independence is Transferrable and is Dependent on the Phospholipase-Containing VP1 Domain of the AAV Capsid To further understand the function of GPR108 for entry and how it engages the capsid, chimeric capsids were used to identify the capsid domain that dictates GPR108 usage. Because AAV5 and AAV2 differ in their GPR108 usage, chimeras generated between these two serotypes were used. A set of reciprocal chimeras with and without the analogous point mutation were designed to determine which region of capsid dictates GPR108 usage (FIG. 14A). These chimeras then were tested in Huh7 WT, AAVR KO, GPR108 KO, or double KO cells with the indicated WT or chimeric capsids (100 μL crude vector prep, plus hAd5 helper virus, CMV.eGPF.T2A.Luciferase transgene). As AAV2 and AAV5 both require AAVR, the expected loss of transduction was observed for all tested serotypes in the AAVR KO and double KO cell lines (FIG. 14B). Interestingly, both of the chimeras containing the VP1 unique region of AAV5 were able to transduce GPR108 Huh7 cells to a similar level as WT cells. Residue 581 did not appear to play a major role in GPR108 usage, although it did have a small effect on overall transduction levels. These experiments demonstrate that the VP1 unique region of AAV dictates GPR108 usage, and that this cellular functionality is transferrable to other AAV serotypes.

Example 12

Further Refined Mapping of the GPR108

Figure 15A:
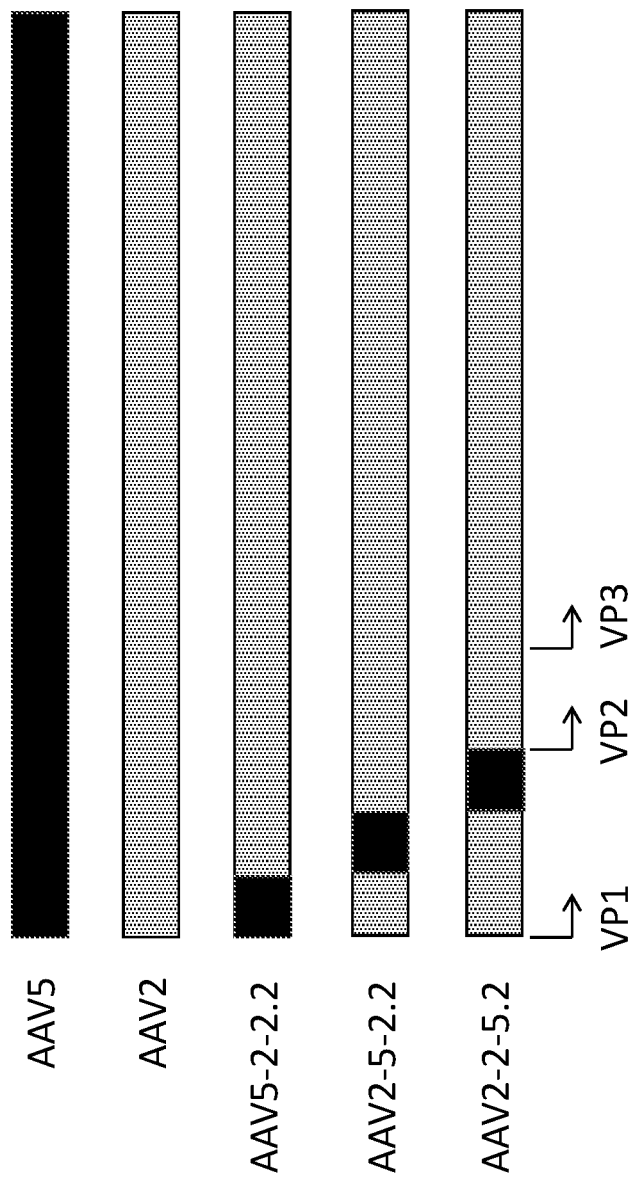
FIG. 15A is a schematic of chimera swaps between portions of AAV5 and AAV2.

Domain swapping experiments were performed to map the GPR108 domain. Specifically, the indicated domains within VP1 from AA5 and AAV2 were exchanged to produce the indicated chimeric AAVs (FIG. 15A). Three different capsid chimeras were synthesized, in which the sequence previously identified to confer GPR108 dependency was broken down into three parts using conserved regions as break points. The GPR108-dependent regions from AAV5 capsid were swapped into the AAV2 capsid and vectors were produced.

Figure 15B:
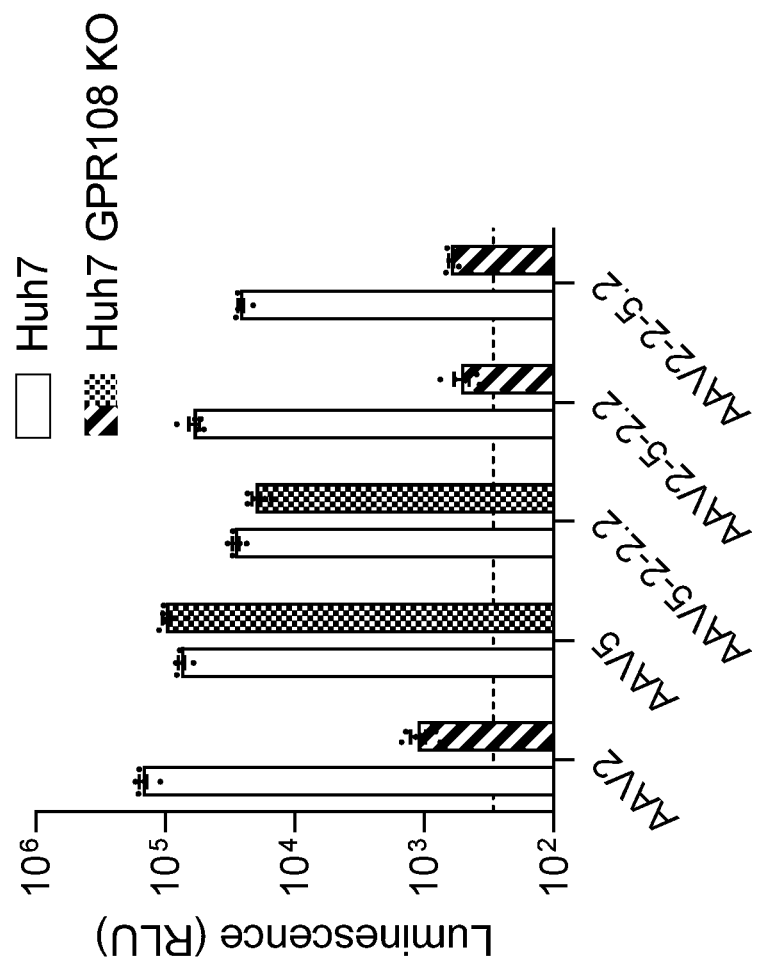
FIG. 15B is a graph showing luciferase expression (RLU/s) in Huh7 and Huh7 GPR108 KO transduced with the indicated AAV 48 hours after transduction. Data are shown as mean±SEM of five technical replicates.

Huh7 cells were transduced with equal volumes of crude virus preparations of wild type AAVs (i.e., AAV2 or AAV5) or chimeric AAVs (i.e., AAV5-2-2.2 (SEQ ID NO:5), AAV2-5-2.2 (SEQ ID NO:6) or AAV2-2-5.2 (SEQ ID NO:7)) expressing GFP.T2A.luciferase transgene as described herein and shown below. The amount of luciferase (RLU/s) in the transformed Huh7 cells was determined 48 hours after transduction and compared with luciferase expression in an Huh7 cell line in which GPR108 has been knocked out (Huh7 GPR108 KO). The results, are shown in FIG. 15B (mean±SEM of 5 replicates).

```
Cap 5-2-2.2
                                                                    (SEQ ID NO: 5)
ATGTCTTTTGTTGATCACCCTCCAGATTGGTTGGAAGAAGTTGGTGAAGGTCTTCGCGAGTTTTT

GGGCCTTGAAGCGGGCCCACCGAAACCAAAACCCAATCAGCAGCATCAAGATCAAGCCCGTGGTC

TTGTGCTTCCTGGGTACAAGTACCTCGGACCCTTCAACGGACTCGACAAGGGAGAGCCGGTCAAC

GAGGCAGACGCCGCGGCCCTCGAGCACGACAAAGCCTACGACCGGCAGCTCGACAGCGGAGACAA

CCCGTACCTCAAGTACAACCACGCCGACGCGGAGTTTCAGGAGCGCCTTAAAGAAGATACGTCTT

TTGGGGGCAACCTCGGACGAGCAGTCTTCCAGGCGAAAAAGAGGGTTCTTGAACCTCTGGGCCTG

GTTGAGGAACCTGTTAAGACGGCTCCGGGAAAAAAGAGGCCGGTAGAGCACTCTCCTGTGGAGCC

AGACTCCTCCTCGGGAACCGGAAAGGCGGGCCAGCAGCCTGCAAGAAAAAGATTGAATTTTGGTC

AGACTGGAGACGCAGACTCAGTACCTGACCCCCAGCCTCTCGGACAGCCACCAGCAGCCCCCTCT

GGTCTGGGAACTAATACGATGGCTACAGGCAGTGGCGCACCAATGGCAGACAATAACGAGGGCGC

CGACGGAGTGGGTAATTCCTCGGGAAATTGGCATTGCGATTCCACATGGATGGGCGACAGAGTCA

TCACCACCAGCACCCGAACCTGGGCCCTGCCCACCTACAACAACCACCTCTACAAACAAATTTCC

AGCCAATCAGGAGCCTCGAACGACAATCACTACTTTGGCTACAGCACCCCTTGGGGGTATTTTGA

CTTCAACAGATTCCACTGCCACTTTTCACCACGTGACTGGCAAAGACTCATCAACAACAACTGGG

GATTCCGACCCAAGAGACTCAACTTCAAGCTCTTTAACATTCAAGTCAAAGAGGTCACGCAGAAT

GACGGTACGACGACGATTGCCAATAACCTTACCAGCACGGTTCAGGTGTTTACTGACTCGGAGTA

CCAGCTCCCGTACGTCCTCGGCTCGGCGCATCAAGGATGCCTCCCGCCGTTCCCAGCAGACGTCT

TCATGGTGCCACAGTATGGATACCTCACCCTGAACAACGGGAGTCAGGCAGTAGGACGCTCTTCA

TTTTACTGCCTGGAGTACTTTCCTTCTCAGATGCTGCGTACCGGAAACAACTTTACCTTCAGCTA

CACTTTTGAGGACGTTCCTTTCCACAGCAGCTACGCTCACAGCCAGAGTCTGGACCGTCTCATGA

ATCCTCTCATCGACCAGTACCTGTATTACTTGAGCAGAACAAACACTCCAAGTGGAACCACCACG

CAGTCAAGGCTTCAGTTTTCTCAGGCCGGAGCGAGTGACATTCGGGACCAGTCTAGGAACTGGCT

TCCTGGACCCTGTTACCGCCAGCAGCGAGTATCAAAGACATCTGCGGATAACAACAACAGTGAAT

ACTCGTGGACTGGAGCTACCAAGTACCACCTCAATGGCAGAGACTCTCTGGTGAATCCGGGCCCG

GCCATGGCAAGCCACAAGGACGATGAAGAAAAGTTTTTTCCTCAGAGCGGGGTTCTCATCTTTGG

GAAGCAAGGCTCAGAGAAAACAAATGTGGACATTGAAAAGGTCATGATTACAGACGAAGAGGAAA

TCAGGACAACCAATCCCGTGGCTACGGAGCAGTATGGTTCTGTATCTACCAACCTCCAGAGAGGC

AACAGACAAGCAGCTACCGCAGATGTCAACACACAAGGCGTTCTTCCAGGCATGGTCTGGCAGGA

CAGAGATGTGTACCTTCAGGGGCCCATCTGGGCAAAGATTCCACACACGGACGGACATTTTCACC

CCTCTCCCCTCATGGGTGGATTCGGACTTAAACACCCTCCTCCACAGATTCTCATCAAGAACACC
```

-continued

CCGGTACCTGCGAATCCTTCGACCACCTTCAGTGCGGCAAAGTTTGCTTCCTTCATCACACAGTA

CTCCACGGGACAGGTCAGCGTGGAGATCGAGTGGGAGCTGCAGAAGGAAAACAGCAAACGCTGGA

ATCCCGAAATTCAGTACACTTCCAACTACAACAAGTCTGTTAATGTGGACTTTACTGTGGACACT

AATGGCGTGTATTCAGAGCCTCGCCCCATTGGCACCAGATACCTGACTCGTAATCTGTAA

Cap 2-5-2.2

(SEQ ID NO: 6)

ATGGCTGCCGATGGTTATCTTCCAGATTGGCTCGAGGACACTCTCTCTGAAGGAATAAGACAGTG

GTGGAAGCTCAAACCTGGCCCACCACCACCAAAGCCCGCAGAGCGGCATAAGGACGACAGCAGGG

GTCTTGTGCTGCCTGGTTATAACTATCTCGGACCCGGAAACGGGCTCGATCGAGGAGAGCCTGTC

AACAGGGCAGACGAGGTCGCGCGAGAGCACGACATCTCGTACAACGAGCAGCTTGAGGCGGGAGA

CAACCCCTACCTCAAGTACAACCACGCCGACGCGGAGTTTCAGGAGCGCCTTAAAGAAGATACGT

CTTTTGGGGGCAACCTCGGACGAGCAGTCTTCCAGGCGAAAAAGAGGGTTCTTGAACCTCTGGGC

CTGGTTGAGGAACCTGTTAAGACGGCTCCGGGAAAAAAGAGGCCGGTAGAGCACTCTCCTGTGGA

GCCAGACTCCTCCTCGGGAACCGGAAAGGCGGGCCAGCAGCCTGCAAGAAAAAGATTGAATTTTG

GTCAGACTGGAGACGCAGACTCAGTACCTGACCCCCAGCCTCTCGGACAGCCACCAGCAGCCCCC

TCTGGTCTGGGAACTAATACGATGGCTACAGGCAGTGGCGCACCAATGGCAGACAATAACGAGGG

CGCCGACGGAGTGGGTAATTCCTCGGGAAATTGGCATTGCGATTCCACATGGATGGGCGACAGAG

TCATCACCACCAGCACCCGAACCTGGGCCCTGCCCACCTACAACAACCACCTCTACAAACAAATT

TCCAGCCAATCAGGAGCCTCGAACGACAATCACTACTTTGGCTACAGCACCCCTTGGGGTATTT

TGACTTCAACAGATTCCACTGCCACTTTTCACCACGTGACTGGCAAAGACTCATCAACAACAACT

GGGGATTCCGACCCAAGAGACTCAACTTCAAGCTCTTTAACATTCAAGTCAAAGAGGTCACGCAG

AATGACGGTACGACGACGATTGCCAATAACCTTACCAGCACGGTTCAGGTGTTTACTGACTCGGA

GTACCAGCTCCCGTACGTCCTCGGCTCGGCGCATCAAGGATGCCTCCCGCCGTTCCCAGCAGACG

TCTTCATGGTGCCACAGTATGGATACCTCACCCTGAACAACGGGAGTCAGGCAGTAGGACGCTCT

TCATTTTACTGCCTGGAGTACTTTCCTTCTCAGATGCTGCGTACCGGAAACAACTTTACCTTCAG

CTACACTTTTGAGGACGTTCCTTTCCACAGCAGCTACGCTCACAGCCAGAGTCTGGACCGTCTCA

TGAATCCTCTCATCGACCAGTACCTGTATTACTTGAGCAGAACAAACACTCCAAGTGGAACCACC

ACGCAGTCAAGGCTTCAGTTTTCTCAGGCCGGAGCGAGTGACATTCGGGACCAGTCTAGGAACTG

GCTTCCTGGACCCTGTTACCGCCAGCAGCGAGTATCAAAGACATCTGCGGATAACAACAACAGTG

AATACTCGTGGACTGGAGCTACCAAGTACCACCTCAATGGCAGAGACTCTCTGGTGAATCCGGGC

CCGGCCATGGCAAGCCACAAGGACGATGAAGAAAAGTTTTTTCCTCAGAGCGGGGTTCTCATCTT

TGGGAAGCAAGGCTCAGAGAAAACAAATGTGGACATTGAAAAGGTCATGATTACAGACGAAGAGG

AAATCAGGACAACCAATCCCGTGGCTACGGAGCAGTATGGTTCTGTATCTACCAACCTCCAGAGA

GGCAACAGACAAGCAGCTACCGCAGATGTCAACACACAAGGCGTTCTTCCAGGCATGGTCTGGCA

GGACAGAGATGTGTACCTTCAGGGGCCCATCTGGGCAAAGATTCCACACACGGACGGACATTTTC

ACCCCTCTCCCCTCATGGGTGGATTCGGACTTAAACACCCTCCTCCACAGATTCTCATCAAGAAC

ACCCCGGTACCTGCGAATCCTTCGACCACCTTCAGTGCGGCAAAGTTTGCTTCCTTCATCACACA

GTACTCCACGGGACAGGTCAGCGTGGAGATCGAGTGGGAGCTGCAGAAGGAAAACAGCAAACGCT

GGAATCCCGAAATTCAGTACACTTCCAACTACAACAAGTCTGTTAATGTGGACTTTACTGTGGAC

ACTAATGGCGTGTATTCAGAGCCTCGCCCCATTGGCACCAGATACCTGACTCGTAATCTGTAA

Cap 2-2-5.2

(SEQ ID NO: 7)

ATGGCTGCCGATGGTTATCTTCCAGATTGGCTCGAGGACACTCTCTCTGAAGGAATAAGACAGTG

GTGGAAGCTCAAACCTGGCCCACCACCACCAAAGCCCGCAGAGCGGCATAAGGACGACAGCAGGG

GTCTTGTCCTTCCTGGGTACAAGTACCTCGGACCCTTCAACGGACTCGACAAGGGAGAGCCGGTC

AACGAGGCAGACGCCGCGGCCCTCGAGCACGACAAAGCCTACGACCGGCAGCTCGACAGCGGAGA

CAACCCGTACCTCAAGTACAACCACGCGGACGCCGAGTTTCAGGAGAAGCTCGCCGACGACACAT

CCTTCGGGGGAAACCTCGGAAAGGCAGTCTTTCAGGCCAAGAAAAGGGTTCTCGAACCTCTGGGC

CTGGTTGAGGAACCTGTTAAGACGGCTCCGGGAAAAAAGAGGCCGGTAGAGCACTCTCCTGTGGA

GCCAGACTCCTCCTCGGGAACCGGAAAGGCGGGCCAGCAGCCTGCAAGAAAAAGATTGAATTTTG

GTCAGACTGGAGACGCAGACTCAGTACCTGACCCCCAGCCTCTCGGACAGCCACCAGCAGCCCCC

TCTGGTCTGGGAACTAATACGATGGCTACAGGCAGTGGCGCACCAATGGCAGACAATAACGAGGG

CGCCGACGGAGTGGGTAATTCCTCGGGAAATTGGCATTGCGATTCCACATGGATGGGCGACAGAG

TCATCACCACCAGCACCCGAACCTGGGCCCTGCCCACCTACAACAACCACCTCTACAAACAAATT

TCCAGCCAATCAGGAGCCTCGAACGACAATCACTACTTTGGCTACAGCACCCCTTGGGGGTATTT

TGACTTCAACAGATTCCACTGCCACTTTTCACCACGTGACTGGCAAAGACTCATCAACAACAACT

GGGGATTCCGACCCAAGAGACTCAACTTCAAGCTCTTTAACATTCAAGTCAAAGAGGTCACGCAG

AATGACGGTACGACGACGATTGCCAATAACCTTACCAGCACGGTTCAGGTGTTTACTGACTCGGA

GTACCAGCTCCCGTACGTCCTCGGCTCGGCGCATCAAGGATGCCTCCCGCCGTTCCCAGCAGACG

TCTTCATGGTGCCACAGTATGGATACCTCACCCTGAACAACGGGAGTCAGGCAGTAGGACGCTCT

TCATTTACTGCCTGGAGTACTTTCCTTCTCAGATGCTGCGTACCGGAAACAACTTTACCTTCAG

CTACACTTTTGAGGACGTTCCTTTCCACAGCAGCTACGCTCACAGCCAGAGTCTGGACCGTCTCA

TGAATCCTCTCATCGACCAGTACCTGTATTACTTGAGCAGAACAAACACTCCAAGTGGAACCACC

ACGCAGTCAAGGCTTCAGTTTTCTCAGGCCGGAGCGAGTGACATTCGGGACCAGTCTAGGAACTG

GCTTCCTGGACCCTGTTACCGCCAGCAGCGAGTATCAAAGACATCTGCGGATAACAACAACAGTG

AATACTCGTGGACTGGAGCTACCAAGTACCACCTCAATGGCAGAGACTCTCTGGTGAATCCGGGC

CCGGCCATGGCAAGCCACAAGGACGATGAAGAAAAGTTTTTTCCTCAGAGCGGGGTTCTCATCTT

TGGGAAGCAAGGCTCAGAGAAAACAAATGTGGACATTGAAAAGGTCATGATTACAGACGAAGAGG

AAATCAGGACAACCAATCCCGTGGCTACGGAGCAGTATGGTTCTGTATCTACCAACCTCCAGAGA

GGCAACAGACAAGCAGCTACCGCAGATGTCAACACACAAGGCGTTCTTCCAGGCATGGTCTGGCA

GGACAGAGATGTGTACCTTCAGGGGCCCATCTGGGCAAAGATTCCACACACGGACGGACATTTTC

ACCCCTCTCCCCTCATGGGTGGATTCGGACTTAAACACCCTCCTCCACAGATTCTCATCAAGAAC

ACCCCGGTACCTGCGAATCCTTCGACCACCTTCAGTGCGGCAAAGTTTGCTTCCTTCATCACACA

GTACTCCACGGGACAGGTCAGCGTGGAGATCGAGTGGGAGCTGCAGAAGGAAAACAGCAAACGCT

GGAATCCCGAAATTCAGTACACTTCCAACTACAACAAGTCTGTTAATGTGGACTTTACTGTGGAC

ACTAATGGCGTGTATTCAGAGCCTCGCCCCATTGGCACCAGATACCTGACTCGTAATCTGTAA

The analysis of transduction in Huh7 and Huh7 GPR108 KO showed that the new capsids were able to transduce wild type cells at similar levels. While the only chimera able to transduce GPR108 KO cells was the one containing the first 4 amino acids of AAV5.

An alignment between the relevant region from the capsid sequence of AAV2 and the relevant region from the capsid sequence of AAV5 was created.

```
Cap2   MAADGYLPDWLEDTLSEGIRQWWKLKPGPPPPKPAERHKDDSRGLV   (SEQ ID NO: 3)
       |:...:.||||: :.||:|:..|:.|||.|||.::|:|.:||||
Cap5   MSFVDHPPDWLEE-VGEGLREFLGLEAGPPKPKPNQQHQDQARGLV   (SEQ ID NO: 4)
```

The region responsible for GPR108 dependency was aligned from a number of different AAVs (FIG. 16), including amino acid sequences from AAV5 as well as a number of GPR108-dependent serotypes (i.e., AAV2, AAV4, AAVrh32.33, AAVanc80L65, AAV1, AAV6.2, AAV8, AAV3, and AAV9). As shown in FIG. 16, this N-terminal sequence is highly conserved among GPR108-dependent serotypes, while AAV5 differs in three main regions (boxed). These regions are likely involved in the dependency to GPR108, and were used to generate a GPR108-independent consensus sequence (SEQ ID NO:1) and a GPR108-dependent consensus sequence (SEQ ID NO:2). Thus, a GPR108-independent AAV includes the following VP1 consensus sequence:

$$MX_1X_2VDHPX_3X_4X_5X_6X_7EVGX_8X_9X_{10}X_{11}X_{12}FLGLEA, \quad \text{(SEQ ID NO: 1)}$$

wherein each of $X_{1-12}$ can be any amino acid; and
a GPR108-dependent AAV includes the following VP1 consensus sequence:

$$MX_1X_2DGYLX_3X_4X_5X_6X_7D(T/N)LSX_8X_9X_{10}X_{11}X_{12}WW(K/A/D)L(K/Q)P, \quad \text{(SEQ ID NO: 2)}$$

wherein each of $X_{1-12}$ can be any amino acid.

Example 13

Stability and Performance Experiments

The stability and performance of AAV2, AAV5, and chimeras of the two were examined in vivo and in vitro.

C57BL/6J mice (5 animals per group) were treated with 1e11 gc/mouse of AAV2, AAV5, AAV2.5, AAV5.2 or PBS (control) carrying the CMV-EGPF.T2A.luciferase transgene. Luciferase expression was examined in the mice ($p/s/cm^2/sr$) for 6 weeks following transformation. FIG. 17A shows the results of these experiments (mean±SEM).

Wildtype MEF cells (WT MEF) or MEF cells derived from GPR108 KO mice (CPR108 KO MEF) were transduced with AAV2, AAV5, AAV2.5 or AAV5.2 viruses carrying the GFP.T2A.luciferase transgene. Cells were treated with 200 pfu/cell of Ad5 for 2 hours before infecting with the AAVs (MOI=1e4). The amount of luciferase (RLU/s) was examined 48 hour after transduction. FIG. 17B shows the results of three independent experiments (mean±SEM).

Figure 17C:
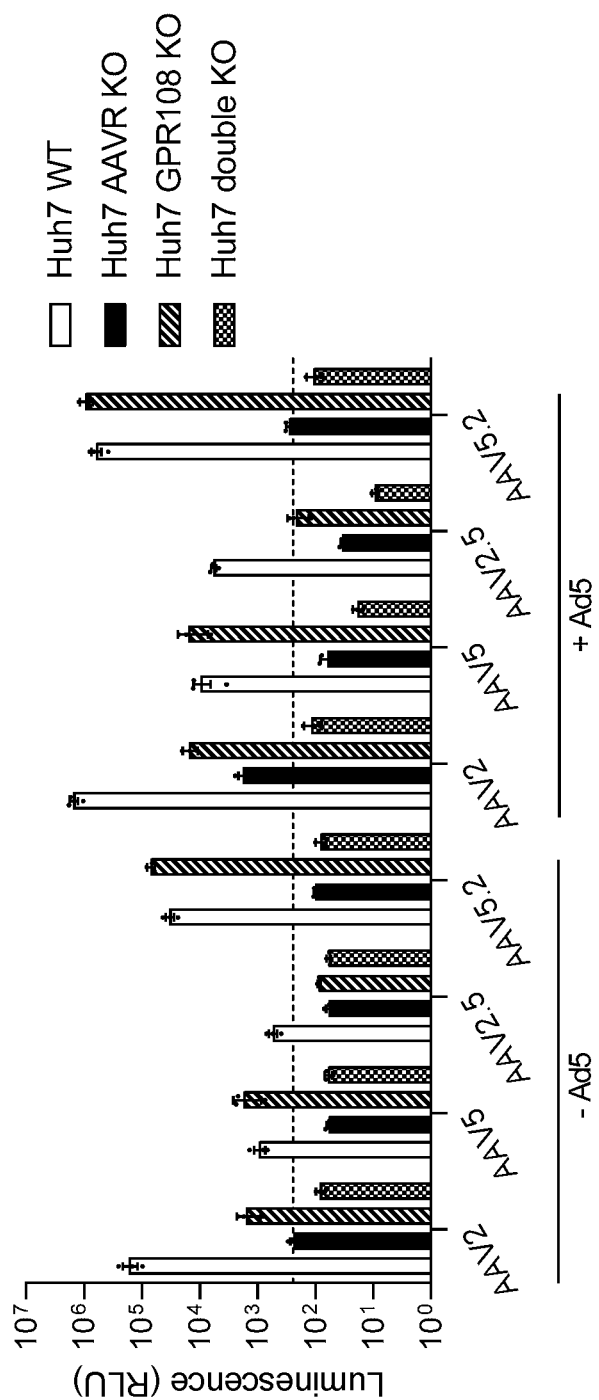
FIG. 17C is a graph of luciferase (RLU/s) in Huh7, Huh7 AAVR KO, Huh7 GPR108 KO or Huh7 double KO transduced with the indicated AAV expressing luciferase 48 h after transduction. Data are shown as mean±SEM of three independent experiments.
Figure 18A:
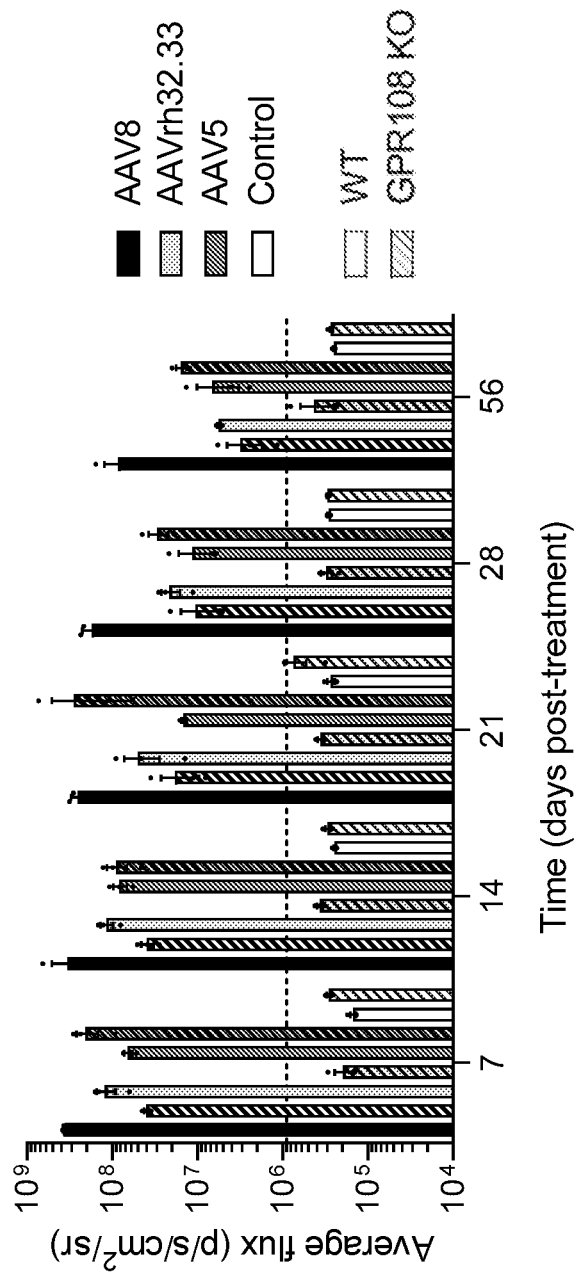
FIG. 18A is a graph of in vivo luciferase expression (p/s/cm2/sr) over 8-weeks following treatment of C57BL/6J and GPR108 KO mice with 1e11gc/mouse of the indicated AAV carrying a luciferase transgene. Data is shown as mean±SEM of three animals per group.
Figure 18B:
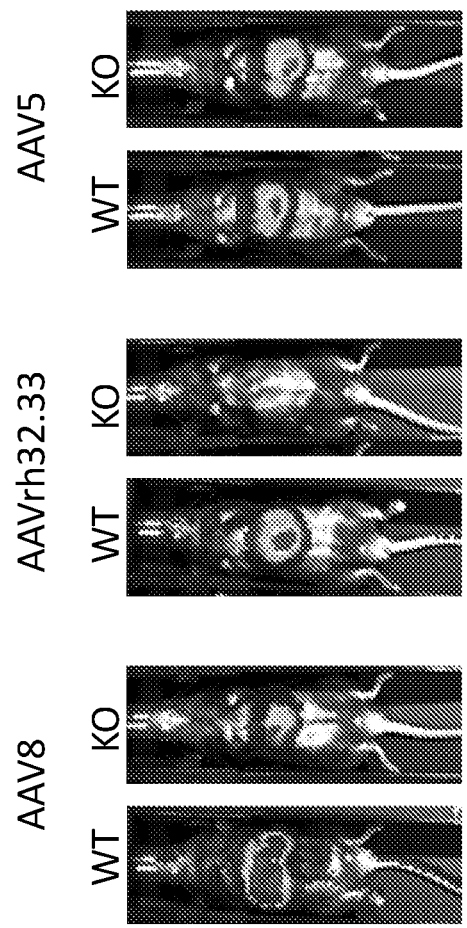
FIG. 18B are images of a representative mice per group at day 14 after the administration of the vectors.

Huh7, Huh7 AAVR KO, Huh7 GPR108 KO or Huh7 double KO were transduced with AAV2, AAV5, AAV2.5 or AAV5.2 viruses carrying the GFP.T2A.luciferase transgene. A set of cells were treated with 200 pfu/cell of Ad5 for 2 hours before infecting with the AAVs (MOI=1e4), while the others were directly treated with the AAVs. The amount of luciferase (RLU/s) was measured 48 hours after transduction. FIG. 17C shows the results of three independent experiments (mean±SEM).

These results demonstrate that AAVs produced using VP1 polypeptides that alter GPR108 dependence are stable structures that can transduce murine MEFs in vitro and mouse tissues in vivo at similar level of the parental wild type vectors.

Example 14

In Vivo Requirement for GPR108

C57BL/6J mice and GPR108 KO mice (3 animals per group) were transduced with 1e11gc/mouse of AAV8, AAVrh32.33, AAV5 viruses (or PBS as a control) carrying the CMV-Luciferase transgene. The amount of luciferase was measured (p/s/cm2/sr; mean±SEM) over a period of 8 weeks following transduction (FIG. 18A). A representative mice from each group was imaged 14 days after transduction with the indicated vector (FIG. 18B). The results shown in FIG. 18A and FIG. 18B demonstrate that GPR108 is a required entry factor for in vivo transduction by AAV.

OTHER EMBODIMENTS

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

This disclosure features methods and compositions that can be used for, can be used in conjunction with, can be used in preparation for, and are products of the disclosed methods and compositions. These and other materials are disclosed herein, and it is understood that combinations, subsets, interactions, groups, etc, of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each combination and permutation of the compositions and the methods are specifically contemplated unless specifically indicated to the contrary. Likewise, any subset or combination of these is also specifically contemplated and disclosed.

What is claimed is:

1. A method of modulating the transduction efficiency of an adeno-associated virus (AAV) into a cell, the method comprising
introducing a genetically-modified adeno-associated virus (AAV) into the cell, wherein the AAV capsid has been genetically modified to comprise a heterologous VP1 polypeptide sequence, wherein the heterologous VP1 polypeptide sequence requires the presence of a GPR108 receptor for transduction or does not require the presence of a GPR108 receptor for transduction of the cell, wherein the heterologous VP1 polypeptide or portion thereof comprises the sequence shown in SEQ ID NO: 18 or 19.

2. The method of claim 1, wherein the heterologous VP1 polypeptide sequence requires the presence of a GPR108 receptor for transduction.

3. The method of claim 1, wherein the heterologous VP1 polypeptide sequence does not require the presence of a GPR108 receptor for transduction of the cell.

4. A method of modifying the cell entry of an adeno-associated virus (AAV), the method comprising:
genetically engineering an AAV to be GPR108-independent, wherein the genetically engineered GPR108-independent AAV comprises a VP1 polypeptide sequence having the sequence SEQ ID NO: 18, or
genetically engineering an AAV to be GPR108-dependent, wherein the genetically engineered GPR108-dependent AAV comprises a VP1 polypeptide sequence having the sequence shown in SEQ ID NO:19,
thereby modifying the cell entry of the AAV.

5. The method of claim 1, wherein the cell is in vivo.

6. The method of claim 1, wherein the cell is selected from the group consisting of a liver cell, a kidney cell, a heart cell, a lung cell, an epithelial cell, an endothelial cell, a bone marrow cell, and a hematopoietic stem cell.

7. A method of increasing the uptake of a heterologous therapeutic agent into a cell, the method comprising contacting the cell with the heterologous therapeutic agent linked to an AAV VP1 polypeptide, wherein the VP1 polypeptide comprises the sequence shown in SEQ ID NO: 18.

8. The method of claim 7, wherein the therapeutic agent is a protein or protein complex.

9. The method of claim 7, wherein the therapeutic agent is further linked to a binding factor that binds to GPR108.

10. The method of claim 9, wherein the binding factor that binds to GPR108 is selected from the group consisting of an antibody, an aptamer, and an antibody domain.

11. A composition comprising a heterologous therapeutic agent linked to a VP1 polypeptide comprising SEQ ID NO:18 or SEQ ID NO: 19.

12. The composition of claim 11, wherein the heterologous therapeutic agent is a protein or protein complex.

13. An AAV capsid sequence comprising a heterologous VP1 sequence that comprises SEQ ID NO: 18.

14. An AAV capsid sequence comprising a heterologous VP1 sequence that comprises SEQ ID NO: 19.

* * * * *

SEQUENCE LISTING

<160> NUMBER OF SEQ ID NOS: 20

<210> SEQ ID NO 1
<211> LENGTH: 26
<212> TYPE: PRT
<213> ORGANISM: Artificial
<220> FEATURE:
<223> OTHER INFORMATION: Synthetically generated protein
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (8)..(12)
<223> OTHER INFORMATION: Xaa can be any naturally occurring amino acid
<220> FEATURE:
<221> NAME/KEY: misc_feature
<222> LOCATION: (16)..(20)
<223> OTHER INFORMATION: Xaa can be any naturally occurring amino acid

<400> SEQUENCE: 1

Met Xaa Xaa Val Asp His Pro Xaa Xaa Xaa Xaa Xaa Glu Val Gly Xaa
1               5                   10                  15

Xaa Xaa Xaa Xaa Phe Leu Gly Leu Glu Ala
            20                  25

<210> SEQ ID NO 2
<211> LENGTH: 27
<212> TYPE: PRT
<213> ORGANISM: Artificial
<220> FEATURE:
<223> OTHER INFORMATION: Synthetically generated protein
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (8)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa = Thr or Asn
<220> FEATURE:
<221> NAME/KEY: misc_feature
<222> LOCATION: (17)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa = Lys, Ala or Asp
<220> FEATURE:
<221> NAME/KEY: misc_feature
<222> LOCATION: (26)..(26)
<223> OTHER INFORMATION: Xaa = Lys or Gln

<400> SEQUENCE: 2

Met Xaa Xaa Asp Gly Tyr Leu Xaa Xaa Xaa Xaa Xaa Asp Xaa Leu Ser
1               5                   10                  15

Xaa Xaa Xaa Xaa Xaa Trp Trp Xaa Leu Xaa Pro
            20                  25

<210> SEQ ID NO 3
<211> LENGTH: 46
<212> TYPE: PRT
<213> ORGANISM: Artificial
<220> FEATURE:
<223> OTHER INFORMATION: Adeno-associated virus

<400> SEQUENCE: 3

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val
        35                  40                  45

<210> SEQ ID NO 4
<211> LENGTH: 45
<212> TYPE: PRT
<213> ORGANISM: Adeno-associated virus

<400> SEQUENCE: 4

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val
        35                  40                  45

<210> SEQ ID NO 5
<211> LENGTH: 2205
<212> TYPE: DNA
<213> ORGANISM: Artificial
<220> FEATURE:
<223> OTHER INFORMATION: Synthetically generated nucleic acid

<400> SEQUENCE: 5
atgtcttttg ttgatcaccc tccagattgg ttggaagaag ttggtgaagg tcttcgcgag       60
tttttgggcc ttgaagcggg cccaccgaaa ccaaaaccca atcagcagca tcaagatcaa      120
gcccgtggtc ttgtgcttcc tgggtacaag tacctcggac ccttcaacgg actcgacaag      180
ggagagccgg tcaacgaggc agacgccgcg gccctcgagc acgacaaagc ctacgaccgg      240
cagctcgaca gcggagacaa cccgtacctc aagtacaacc acgccgacgc ggagtttcag      300
gagcgcctta agaagatac gtcttttggg ggcaacctcg acgagcagt cttccaggcg       360 aaaaagaggg ttcttgaacc tctgggcctg gttgaggaac ctgttaagac ggctccggga      420
aaaaagaggc cggtagagca ctctcctgtg gagccagact cctcctcggg aaccggaaag      480
gcgggccagc agcctgcaag aaaaagattg aattttggtc agactggaga cgcagactca      540
gtacctgacc cccagcctct cggacagcca ccagcagccc cctctggtct gggaactaat      600
acgatggcta caggcagtgg cgcaccaatg cagacaata cgagggcgc cgacggagtg       660 ggtaattcct cgggaaattg gcattgcgat tccacatgga tgggcgacag agtcatcacc      720
accagcaccc gaacctgggc cctgcccacc tacaacaacc acctctacaa acaaatttcc      780
agccaatcag gagcctcgaa cgacaatcac tactttggct acagcacccc ttggggggtat      840 tttgacttca acagattcca ctgccacttt tcaccacgtg actggcaaag actcatcaac      900
aacaactggg gattccgacc caagagactc aacttcaagc tctttaacat tcaagtcaaa      960
gaggtcacgc agaatgacgg tacgacgacg attgccaata accttaccag cacggttcag     1020
gtgtttactg actcggagta ccagctcccg tacgtcctcg gctcggcgca tcaaggatgc     1080
ctcccgccgt tcccagcaga cgtcttcatg gtgccacagt atggataccl caccctgaac     1140 aacgggagtc aggcagtagg acgctcttca ttt actgcc tggagtactt tccttctcag     1200
atgctgcgta ccggaaacaa ctttaccttc agctacactt tgaggacgt tccttccac      1260

```
agcagctacg ctcacagcca gagtctggac cgtctcatga atcctctcat cgaccagtac   1320
ctgtattact tgagcagaac aaacactcca agtggaacca ccacgcagtc aaggcttcag   1380
ttttctcagg ccggagcgag tgacattcgg gaccagtcta ggaactggct tcctggaccc   1440
tgttaccgcc agcagcgagt atcaaagaca tctgcggata caacaacag tgaatactcg    1500 tggactggag ctaccaagta ccacctcaat ggcagagact ctctggtgaa tccgggcccg   1560
gccatggcaa gccacaagga cgatgaagaa aagttttttc ctcagagcgg ggttctcatc   1620
tttgggaagc aaggctcaga gaaaacaaat gtggacattg aaaaggtcat gattacagac   1680
gaagaggaaa tcaggacaac caatcccgtg gctacggagc agtatggttc tgtatctacc   1740
aacctccaga gaggcaacag acaagcagct accgcagatg tcaacacaca aggcgttctt   1800
ccaggcatgg tctggcagga cagagatgtg taccttcagg ggcccatctg ggcaaagatt   1860
ccacacacgg acggacattt tcacccctct cccctcatgg gtggattcgg acttaaacac   1920
cctcctccac agattctcat caagaacacc ccggtacctg cgaatccttc gaccaccttc   1980
agtgcggcaa agtttgcttc cttcatcaca cagtactcca cggacaggt cagcgtggag    2040 atcgagtggg agctgcagaa ggaaaacagc aaacgctgga atcccgaaat tcagtacact   2100
tccaactaca caagtctgt taatgtggac tttactgtgg acactaatgg cgtgtattca    2160
gagcctcgcc ccattggcac cagatacctg actcgtaatc tgtaa                   2205

<210> SEQ ID NO 6
<211> LENGTH: 2208
<212> TYPE: DNA
<213> ORGANISM: Artificial
<220> FEATURE:
<223> OTHER INFORMATION: Synthetically generated nucleic acid

<400> SEQUENCE: 6
atggctgccg atggttatct tccagattgg ctcgaggaca ctctctctga aggaataaga    60
cagtggtgga agctcaaacc tggcccacca ccaccaaagc ccgcagagcg gcataaggac   120
gacagcaggg gtcttgtgct gcctggttat aactatctcg gacccggaaa cgggctcgat   180
cgaggagagc ctgtcaacag ggcagacgag gtcgcgcgag agcacgacat tcgtacaaac   240
gagcagcttg aggcgggaga caaccctac ctcaagtaca ccacgccga cgcggagttt     300 cagggagcgc ttaaagaaga tacgtctttt gggggcaacc tcggacgagc agtcttccag   360
gcgaaaaaga gggttcttga acctctgggc ctggttgagg aacctgttaa gacggctccg   420
ggaaaaaaga ggccggtaga gcactctcct gtggagccag actcctcctc gggaaccgga   480
aaggcgggcc agcagcctgc aagaaaaaga ttgaattttg gtcagactgg agacgcagac   540
tcagtacctg acccccagcc tctcggacag ccaccagcag cccctctgg tctgggaact    600 aatacgatgg ctacaggcag tggcgcacca atggcagaca ataacgaggg cgccgacgga   660
gtgggtaatt cctcgggaaa ttggcattgc gattccacat ggatgggcga cagagtcatc   720
accaccagca cccgaacctg gccctgccc acctacaaca accacctcta caaacaaatt    780
tccagccaat caggagcctc gaacgacaat cactactttg ctacagcac ccctgggggg    840 tattttgact tcaacagatt ccactgccac ttttcaccac gtgactggca agactcatc    900 aacaacaact ggggattccg acccaagaga ctcaacttca gctctttaa cattcaagtc    960 aaagaggtca cgcagaatga cggtacgacg acgattgcca ataacctta cagcacggtt   1020 caggtgtta ctgactcgga gtaccagctc ccgtacgtcc tcggctcggc gcatcaagga    1080
tgcctcccgc cgttcccagc agacgtcttc atggtgccac agtatggata cctcaccctg   1140
```

-continued

```
aacaacggga gtcaggcagt aggacgctct tcattttact gcctggagta ctttccttct    1200
cagatgctgc gtaccggaaa caactttacc ttcagctaca cttttgagga cgttcctttc    1260
cacagcagct acgctcacag ccagagtctg daccgtctca tgaatcctct catcgaccag    1320
tacctgtatt acttgagcag aacaaacact ccaagtggaa ccaccacgca gtcaaggctt    1380
cagttttctc aggccggagc gagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt ttcctcagag cggggttctc    1620
atctttggga agcaaggctc agagaaaaca aatgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca ttttcacccc tctcccctca tgggtggatt cggacttaaa    1920
caccctcctc cacagattct catcaagaac accccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatcccga aattcagtac    2100
acttccaact acaacaagtc tgttaatgtg gactttactg tggacactaa tggcgtgtat    2160
tcagagcctc gccccattgg caccagatac ctgactcgta atctgtaa                 2208
```

<210> SEQ ID NO 7
<211> LENGTH: 2208
<212> TYPE: DNA
<213> ORGANISM: Artificial
<220> FEATURE:
<223> OTHER INFORMATION: Synthetically generated nucleic acid

<400> SEQUENCE: 7

```
atggctgccg atggttatct tccagattgg ctcgaggaca ctctctctga aggaataaga     60
cagtggtgga agctcaaacc tggcccacca ccaccaaagc ccgcagagcg gcataaggac    120
gacagcaggg gtcttgtgct tcctgggtac aagtacctcg dacccttcaa cggactcgac    180
aagggagagc cggtcaacga ggcagacgcc gcggccctcg agcacgacaa agcctacgac    240
cggcagctcg acagcggaga caacccgtac ctcaagtaca accacgcgga cgccgagttt    300
caggagaagc tcgccgacga cacatccttc ggggdaaacc tcggaaaggc agtctttcag    360
gccaagaaaa gggttctcga acctctgggc ctggttgagg aacctgttaa gacggctccg    420
ggaaaaaaga ggccggtaga gcactctcct gtggagccag actcctcctc gggaaccgga    480
aaggcgggcc agcagcctgc aagaaaaaga ttgaattttg gtcagactgg agacgcagac    540
tcagtacctg acccccagcc tctcggacag ccaccagcag cccctctgg tctgggaact    600
aatacgatgg ctacaggcag tggcgcacca atggcagaca ataacgaggg cgccgacgga    660
gtgggtaatt cctcgggaaa ttggcattgc gattccacat ggatgggcga cagagtcatc    720
accaccagca cccgaacctg ggccctgccc acctacaaca accacctcta caaacaaatt    780
tccagccaat caggagcctc gaacgacaat cactactttg gctacagcac cccttggggg    840
tattttgact tcaacagatt ccactgccac ttttcaccac gtgactggca agactcatc    900
aacaacaact ggggattccg acccaagaga ctcaacttca agctctttaa cattcaagtc    960
```

-continued

```
aaagaggtca cgcagaatga cggtacgacg acgattgcca ataaccttac cagcacggtt    1020
caggtgttta ctgactcgga gtaccagctc ccgtacgtcc tcggctcggc catcaagga     1080 tgcctcccgc cgttcccagc agacgtcttc atggtgccac agtatggata cctcaccctg    1140
aacaacggga gtcaggcagt aggacgctct tcattttact gcctggagta ctttccttct    1200
cagatgctgc gtaccggaaa caactttacc ttcagctaca cttttgagga cgttcctttc    1260
cacagcagct acgctcacag ccagagtctg gaccgtctca tgaatcctct catcgaccag    1320
tacctgtatt acttgagcag aacaaacact ccaagtggaa ccaccacgca gtcaaggctt    1380
cagttttctc aggccggagc gagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt tccctcagag cggggttctc    1620
atctttggga agcaaggctc agagaaaaca aatgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca tttttcaccc tctcccctca tgggtggatt cggacttaaa    1920
caccctcctc cacagattct catcaagaac acccccgtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatcccga aattcagtac    2100
acttccaact acaacaagtc tgttaatgtg gactttactg tggacactaa tggcgtgtat    2160
tcagagcctc gccccattgg caccagatac ctgactcgta atctgtaa                 2208
```

<210> SEQ ID NO 8
<211> LENGTH: 46
<212> TYPE: PRT
<213> ORGANISM: Adeno-associated virus 5

<400> SEQUENCE: 8

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu
        35                  40                  45

<210> SEQ ID NO 9
<211> LENGTH: 47
<212> TYPE: PRT
<213> ORGANISM: Adeno-associated virus 2

<400> SEQUENCE: 9

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu
        35                  40                  45

<210> SEQ ID NO 10
<211> LENGTH: 46

-continued

```
<212> TYPE: PRT
<213> ORGANISM: Adeno-associated virus 4

<400> SEQUENCE: 10

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu
        35                  40                  45

<210> SEQ ID NO 11
<211> LENGTH: 47
<212> TYPE: PRT
<213> ORGANISM: Adeno-associated virus rh32.33

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu
        35                  40                  45

<210> SEQ ID NO 12
<211> LENGTH: 47
<212> TYPE: PRT
<213> ORGANISM: Artificial
<220> FEATURE:
<223> OTHER INFORMATION: Synthetically generated protein

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu
        35                  40                  45

<210> SEQ ID NO 13
<211> LENGTH: 47
<212> TYPE: PRT
<213> ORGANISM: Adeno-associated virus 1

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu
        35                  40                  45

<210> SEQ ID NO 14
<211> LENGTH: 47
<212> TYPE: PRT
<213> ORGANISM: Adeno-associated virus 6.2

<400> SEQUENCE: 14

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
```

```
                    20                  25                  30

Lys Ala Asn Gln Gln Lys Gln Asp Asp Gly Arg Gly Leu Val Leu
        35                  40                  45

<210> SEQ ID NO 15
<211> LENGTH: 47
<212> TYPE: PRT
<213> ORGANISM: Adeno-associated virus 8

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                    20                  25                  30

Lys Ala Asn Gln Gln Lys Gln Asp Asp Gly Arg Gly Leu Val Leu
        35                  40                  45

<210> SEQ ID NO 16
<211> LENGTH: 47
<212> TYPE: PRT
<213> ORGANISM: Adeno-associated virus 3

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
                    20                  25                  30

Lys Ala Asn Gln Gln His Gln Asp Asn Arg Arg Gly Leu Val Leu
        35                  40                  45

<210> SEQ ID NO 17
<211> LENGTH: 47
<212> TYPE: PRT
<213> ORGANISM: Adeno-associated virus 9

<400> SEQUENCE: 17

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                    20                  25                  30

Lys Ala Asn Gln Gln His Gln Asp Asn Ala Arg Gly Leu Val Leu
        35                  40                  45

<210> SEQ ID NO 18
<211> LENGTH: 26
<212> TYPE: PRT
<213> ORGANISM: Artificial
<220> FEATURE:
<223> OTHER INFORMATION: Synthetically generated protein

<400> SEQUENCE: 18

Met Ala Ala Val Asp His Pro Pro Asp Trp Leu Glu Glu Val Gly Glu
1               5                   10                  15

Gly Ile Arg Glu Phe Leu Gly Leu Glu Ala
                    20                  25

<210> SEQ ID NO 19
<211> LENGTH: 27
<212> TYPE: PRT
<213> ORGANISM: Artificial
<220> FEATURE:
<223> OTHER INFORMATION: Synthetically generated protein
```

```
<400> SEQUENCE: 19

Met Ser Phe Asp Gly Tyr Leu Pro Asp Trp Leu Glu Asp Thr Leu Ser
1               5                   10                  15

Glu Gly Leu Arg Glu Trp Trp Lys Leu Lys Pro
            20                  25

<210> SEQ ID NO 20
<211> LENGTH: 19
<212> TYPE: RNA
<213> ORGANISM: Artificial
<220> FEATURE:
<223> OTHER INFORMATION: Synthetically generated nucleic acid

<400> SEQUENCE: 20
cggacaagcc cauuuggaa                                              19
```

UNITED STATES PATENT AND TRADEMARK OFFICE
CERTIFICATE OF CORRECTION

| | | |
|---|---|---|
| PATENT NO. | : 12,195,745 B2 | Page 1 of 1 |
| APPLICATION NO. | : 17/269955 | |
| DATED | : January 14, 2025 | |
| INVENTOR(S) | : Luk H. Vandenberghe, Amanda Dudek and Nerea Zabaleta Lasarte | |

It is certified that error appears in the above-identified patent and that said Letters Patent is hereby corrected as shown below:

On the Title Page

In Line 2 of the Abstract Item (57), delete "vims" and insert -- virus --

Signed and Sealed this
Eighth Day of April, 2025

Coke Morgan Stewart
*Acting Director of the United States Patent and Trademark Office*